(12) United States Patent
Shen et al.

(10) Patent No.: US 9,085,568 B2
(45) Date of Patent: Jul. 21, 2015

(54) MINERALOCORTICOID RECEPTOR ANTAGONISTS

(71) Applicant: Merck Sharp & Dohme Corp., Rahway, NJ (US)

(72) Inventors: Hong Shen, Pudong (CN); Jason M. Cox, East Windsor, NJ (US); Hong Dong Chu, Livingston, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/350,930

(22) PCT Filed: Oct. 8, 2012

(86) PCT No.: PCT/US2012/059170
§ 371 (c)(1),
(2) Date: Apr. 10, 2014

(87) PCT Pub. No.: WO2013/055608
PCT Pub. Date: Apr. 18, 2013

(65) Prior Publication Data
US 2014/0275133 A1     Sep. 18, 2014

Related U.S. Application Data

(60) Provisional application No. 61/546,774, filed on Oct. 13, 2011.

(51) Int. Cl.
| | |
|---|---|
| C07D 413/04 | (2006.01) |
| C07D 413/14 | (2006.01) |
| A61K 31/506 | (2006.01) |
| A61K 31/4439 | (2006.01) |
| A61K 31/422 | (2006.01) |
| A61K 31/4245 | (2006.01) |
| A61K 31/454 | (2006.01) |
| C07D 263/44 | (2006.01) |

(52) U.S. Cl.
CPC ............ *C07D 413/04* (2013.01); *A61K 31/422* (2013.01); *A61K 31/4245* (2013.01); *A61K 31/4439* (2013.01); *A61K 31/454* (2013.01); *A61K 31/506* (2013.01); *C07D 413/14* (2013.01); *C07D 263/44* (2013.01)

(58) Field of Classification Search
CPC ............... C07D 413/04; C07D 413/14; A61K 31/4245; A61K 31/422; A61K 31/4439; A61K 31/506
See application file for complete search history.

(56) References Cited

U.S. PATENT DOCUMENTS

| | | | |
|---|---|---|---|
| 2,366,221 A * | 1/1945 | Spurlock | .................. 548/315.1 |
| 4,298,745 A | 11/1981 | Wootton et al. | |
| 4,337,262 A | 6/1982 | Whittaker et al. | |
| 4,705,864 A | 11/1987 | Cesa et al. | |
| 2004/0067996 A1 | 4/2004 | Sheppeck et al. | |
| 2005/0159413 A1 | 7/2005 | Noe et al. | |
| 2010/0184646 A1 | 7/2010 | Dong et al. | |

FOREIGN PATENT DOCUMENTS

| | | |
|---|---|---|
| EP | 1256571 B1 | 2/2006 |
| WO | WO02017895 A1 | 7/2002 |
| WO | WO2007004037 A1 | 1/2007 |

OTHER PUBLICATIONS

International Search Report for PCT/US2012/059168 mailed on. Dec. 4, 2012; 2 pages.
Written Opinion for PCT/US2012/059168 mailed on Dec. 4, 2012; 2 pages.
International Search Report for PCT/US2012/059170 mailed on Dec. 4, 2012; 2 pages.
Written Opinion for PCT/US2012/059170 mailed on Dec. 4, 2012; 2 pages.
International Search Report for PCT/US2012/059165 mailed on Dec. 17, 2012; 2 pages.
Written Opinion for PCT/US2012/059165 mailed on Dec. 17, 2012; 2 pages.
Knaggs, et al. "Biotransformation of Alosetron: Mechanism of Hydantioin Formation", Tetrahedron Letters, 1995, vol. 36, No. 3, pp. 477-480.

(Continued)

*Primary Examiner* — Matthew Coughlin
(74) *Attorney, Agent, or Firm* — Patricia A. Shatynski; Catherine D. Fitch

(57) ABSTRACT

The present invention is directed to compounds of the Formula (I) as well as pharmaceutically acceptable salts thereof that are possible useful for treating aldosterone-mediated diseases. The invention furthermore relates to processes for preparing compounds of the Formula (I), to their possible use for the treatment of the above mentioned diseases and for preparing pharmaceuticals for this purpose, and to pharmaceutical compositions which comprise compounds of the Formula (I).

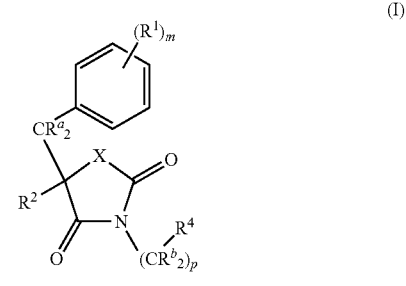

13 Claims, No Drawings

(56) References Cited

OTHER PUBLICATIONS

Sergent, et al., "Synthesis of hydantoin analogues of (2S,3R,4S)-4-hydroxyisoleucine with insulinotropic properties", Bioorganic & Medicinal Chemistry Letters, 18 (2008); pp. 4332-4335.

Castren, et al., "A Functional Promoter Directing Expression of a Novel Type of Rat Mineralocorticoid Receptor mRNA in Brain", Journal of Neuroendocrinology, 3 (1993), pp. 461-466.

Pitt, B., et al., "Eplerenone, a Selective Aldosterone Blocker, in Patients with Left Ventricular Dysfunction after Myocardial Infarction", N. Engl. J. Med., 348 (14); pp. 1309-1321. 2003.

Funder, JW., "Eplerenone in chronic renal disease: the EVALUATE trial", Hypertens. Res., 33 (6); pp. 539-540. 2010.

Gaddam, K., et al. "Rapid Reversal of Left Ventricular Hypertrophy and Intracardiac Volume Overload in patients with resistant hypertension and hyperaldosteronism: a prospective clinival study", Hypertension, 55 (5); pp. 1137-1142. 2010.

Brilla, C.G., et al., "Anti-aldosterone treatment and the prevention of Myocardial Fibrosis in Primary and Secondary Hyperaldosteronism", Journal of Molecular and Cellular Cardiology, (1993) 25 (5), pp. 563-75.

Huang, B.S., et al., "Central neuronal activation and pressor responses induced by circulating ANG II: role of the brain aldosterone-"ouabain" pathway", Am J Physiol Heart Circ Physiol (2010) 2: H422-H430.

Nishizaka, M., et al., "The Role of Aldosterone Antagonists in the Management of Resistant Hypertension", Curr. Hypertens Rep., Oct. 2005; 7(5); pp. 343-347.

Pitt, B., et al., "The Effect of Spironolactone on Morbidity and Mortality in Patients With Severe Heart Failure", (1999); 341 (10); The New England Journal of Medicine, pp. 709-717.

Pitt, B., et al., "Serum Potassium and Clinical Outcomes in the Eplerenone Post-Acute Myocardial Infarction Heart Failure Efficacy and Survival Study (EPHESUS)". Circulation. 2008;118: pp. 1643-1650.

Takai, S., et al., "Eplerenone Inhibits Atherosclerosis in Nonhuman Primates", Hypertension. 2005;46: pp. 1135-1139.

Tirosh, A., "Mineralocorticoid Receptor Antagonists and the Metabolic Syndrome", Curr Hypertens Rep (2010) 12:pp. 252-257.

Williams, J., "Hypertension: Spironolactone and resistant hypertension", Nat. Rev. Endocrinol., May 2010; 6 (5); pp. 248-250.

Zannad, F., "Rationale and design of the Eplerenone in Mild Patients Hospitalization And Survival Study in Heart Failure (EMPHASIS-HF)" European Journal of Heart Failure (2010) 12, pp. 617-622.

* cited by examiner

MINERALOCORTICOID RECEPTOR ANTAGONISTS

RELATED APPLICATIONS

This application claims benefit to provisional application U.S. Ser. No. 61/546,774, filed on 13 Oct. 2011, herein incorporated by reference.

BACKGROUND OF THE INVENTION

The Mineralocorticoid Receptor (MR) is a nuclear hormone receptor that is activated by aldosterone and regulates the expression of many genes involved in electrolyte homeostasis and cardiovascular disease. Increased circulating aldosterone increases blood pressure through its effects on natriuresis, with potentially additional effects on the brain, heart and vasculature. In addition, hyperaldosteronism have been linked to many pathophysiological processes resulting in renal and cardiovascular disease. While hyperaldosteronism is commonly caused by aldosterone-producing adenomas, resistant hypertensive patients frequently suffer from increased aldosterone levels often termed as "Aldosterone Breakthrough" as a result of increases in serum potassium or residual AT1R activity. Hyperaldosteronism and aldosterone breakthrough typically results in increased MR activity and MR antagonists have been shown to be effective as antihypertensive agents and also in the treatment of heart failure and primary hyperaldosteronism.

In addition, in visceral tissues, such as the kidney and the gut, MR regulates sodium retention, potassium excretion and water balance in response to aldosterone. MR expression in the brain also appears to play a role in the control of neuronal excitability, in the negative feedback regulation of the hypothalamic-pituitary-adrenal axis, and in the cognitive aspects of behavioral performance (Castren et al., J. of Neuroendocrinology, 3, 461-66 (1993)).

Eplerenone and spironolactone are two MR antagonists that have been shown to be efficacious in treating cardiovascular disease, particularly hypertension and heart failure (RALES Investigators (1999) The Effect of Spironolactone on Morbidity and Mortality in Patients with Severe Heart Failure, N. Engl. J. Med., 1999, 341(10):709-717; Pitt B, et al., EPHESUS investigator (2003) Eplerenone, a Selective Aldosterone Blocker, in Patients with Left Ventricular Dysfunction After Myocardial Infarction, N. Engl. J. Med., 348 (14):1309-1321; Funder J W., (2010) Eplerenone in Chronic Renal Disease: the EVALUATE trial, Hypertens. Res., 33(6): 539-40.). Moreover, multiple studies have shown that treatment with spironolactone or eplerenone significantly lower systolic blood pressure in mild-moderate, obese, systolic, PHA, and resistant hypertensive patients (Calhoun D A, et al., (2008) Effectiveness of the Selective Aldosterone Blocker, Eplerenone, in Patients with Resistant Hypertension, J. Am. Soc. Hypertens., 2008 November-December; 2(6):462-8; Huang B S, et al., (2010) Central Neuronal Activation and Pressor Responses Induced by Circulating ANG II: role of the brain aldosterone-"ouabain" pathway, Am. J. Physiol. Heart. Circ. Physiol., (2):H422-30; The RALES Investigators. (1996) Effectiveness of Spironolactone added to an Angiotensin-converting enzyme Inhibitor and a Loop Diuretic for Severe Chronic Congestive Heart Failure, (The Randomized Aldactone Evaluation Study [RALES]), Am. J. Cardiol., 1996; 78:902-907; Pitt B, et al., EPHESUS Investigators, Serum potassium and clinical outcomes in the Eplerenone Post-Acute Myocardial Infarction Heart Failure Efficacy and Survival Study (EPHESUS), Circulation, 2008 Oct. 14; 118 (16):1643-50; Bomback A S et al., (2009), Low-dose spironolactone, added to long-term ACE inhibitor therapy, reduces blood pressure and urinary albumin excretion in obese patients with hypertensive target organ damage, Clin. Nephrol., 72(6):449-56; Williams J S, Hypertension: spironolactone and resistant hypertension, Nat. Rev. Endocrinol., 2010 May; 6(5):248-50; Nishizaka M K, et al., The role of aldosterone antagonists in the management of resistant hypertension. Curr Hypertens Rep. 2005 October; 7(5):343-7. Review; Gaddam K, et al., (2010) Rapid reversal of left ventricular hypertrophy and intracardiac volume overload in patients with resistant hypertension and hyperaldosteronism: a prospective clinical study, Hypertension, 55(5):1137-42; Zannad F, et al., (2010) Rationale and design of the Eplerenone in Mild Patients Hospitalization And Survival Study in Heart Failure (EMPHASIS-HF), Eur. J. Heart Fail., 12(6):617-22).

Evidence in preclinical models also suggests that MR antagonists would be efficacious in treating the metabolic syndrome and atherosclerosis (Takai, S. et al, (2005) Eplerenone inhibits atherosclerosis in nonhuman primates. Hypertension. 46(5):1135-9; Tirosh, A. et al., GK. (2010) Mineralocorticoid receptor antagonists and the metabolic syndrome. Curr Hypertens Rep. 2010 August; 12(4):252-7).

Also, published PCT application WO 2002/17895 disclosed that aldosterone antagonists are useful in the treatment of subjects suffering from one or more cognitive dysfunctions including, but not limited to psychoses, cognitive disorders (such as memory disturbances), mood disorders (such as depression and bipolar disorder), anxiety disorders and personality disorders.

Elevation in aldosterone levels, or excess stimulation of mineralocorticoid receptors, is linked to several physiological disorders or pathologic disease states, including Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels. (Hadley, M. E., ENDOCRINOLOGY, $2^{nd}$ Ed., pp. 366-81, (1988); and Brilla et al., Journal of Molecular and Cellular Cardiology, 25 (5), pp. 563-75 (1993). Compounds and/or pharmaceutical compositions which act as MR antagonists might be expected to be of value in the treatment of any of the above conditions. Despite significant therapeutic advances in the treatment of hypertension and heart failure, the current standard of care is suboptimal and there is a clear unmet medical need for additional therapeutic/pharmacological interventions. This invention addresses those needs by providing compounds and compositions, which antagonize the MR and potentially have utility in the treatment or prevention of hypertension, heart failure, other cardiovascular disorders and other aldosterone disorders.

SUMMARY OF THE INVENTION

The present invention relates to compounds which have Mineralocorticoid

Receptor (MR) antagonist activity, which might be expected to be valuable pharmaceutically active compounds for the possible treatment of diseases, for example for treating aldosterone-mediated disorders, including cardiovascular disease. The present invention is directed to compounds of the Formula I:

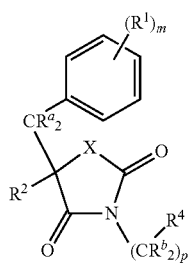

or a pharmaceutically acceptable salt thereof. The invention furthermore relates to possible methods of treating and preventing the above mentioned diseases and to processes for preparing compounds of the Formula I and for pharmaceutical preparations which comprise compounds of Formula I.

DETAILED DESCRIPTION OF THE INVENTION

The invention concerns compounds of Formula I:

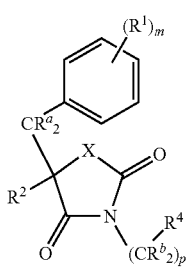

or a pharmaceutically acceptable salt thereof, wherein
X is NH or O;
Each $R^1$ is independently halo, $CF_3$, $C_1$-$C_6$ alkyl, $C_3$-$C_{10}$ cycloalkyl, or OR, wherein said alkyl and cycloalkyl are optionally substituted with one to three groups selected from halo, OR, $CF_3$, or CN;
Each R is independently H, $C_1$-$C_6$ alkyl, $C_3$-$C_{10}$ cycloalkyl, or $CF_3$ wherein said alkyl and cycloalkyl are optionally substituted with one to three groups selected from halo, OH, $C_1$-$C_6$ alkoxy, $CF_3$, or CN;
Each $R^a$ is independently H, $C_1$-$C_6$ alkyl, $C_3$-$C_{10}$ cycloalkyl, or $CF_3$ wherein said alkyl, cycloalkyl and aryl are optionally substituted with one to three groups selected from halo, OR, $CF_3$, or CN;
Each $R^b$ is independently H, $C_1$-$C_6$ alkyl, $C_3$-$C_{10}$ cycloalkyl, $CF_3$, or aryl, wherein said alkyl, cycloalkyl and aryl are optionally substituted with one to three groups selected from halo, OR, $CF_3$, or CN;
$R^2$ is triazolyl, oxadiazolyl, imidazolyl, thiazolyl, pyrazolyl, isoxazolyl, thiadiazolyl or oxazolyl, where triazolyl, oxadiazolyl, imidazolyl, thiazolyl, pyrazolyl, isoxazolyl, thiadiazolyl or oxazolyl is optionally substituted with one to two groups from $R^5$;
$R^4$ is H, $C_1$-$C_6$ alkyl, aryl, or $C_3$-$C_{10}$ cycloalkyl, where said alkyl, aryl, or cycloalkyl is optionally substituted with one to four groups selected from halo or OR;
Each $R^5$ is independently OR, $(CR^c_2)_{0-3}$—$CF_3$, $C_1$-$C_6$ alkyl, $(CR^c_2)_{0-3}$—$C_3$-$C_{10}$ cycloalkyl, $(CR^c_2)_{0-3}$-aryl, $(CR^c_2)_{0-3}$-heteroaryl, or $(CR^c_2)_{0-3}$-halo, where said alkyl, cycloalkyl, aryl or heteroaryl is optionally substituted with one to three groups selected from optionally substituted aryl, optionally substituted heteroaryl, optionally substituted heterocyclyl, OR, halo, $CF_3$ or $NH_2$; and wherein said optionally substituted aryl, optionally substituted heteroaryl, or optionally substituted heterocyclyl are optionally substituted one to four times by halo, $CF_3$, $NH_2$ or OR.
Each $R^c$ is independently H, $C_1$-$C_6$ alkyl, or $C_3$-$C_{10}$ cycloalkyl, wherein said alkyl and cycloalkyl are optionally substituted with one to three groups selected from halo, OR, $CF_3$, or CN;
m is 0, 1, 2 or 3; and
p is 0, 1, 2 or 3.
In another embodiment of the compounds of Formula I or their pharmaceutically acceptable salts,
X is NH or O;
Each $R^1$ is independently halo, $CF_3$, $C_1$-$C_6$ alkyl, $C_3$-$C_{10}$ cycloalkyl, or OR, wherein said alkyl and cycloalkyl are optionally substituted with one to three groups selected from halo, OR, $CF_3$, or CN;
Each R is independently H, $C_1$-$C_6$ alkyl, $C_3$-$C_{10}$ cycloalkyl, or $CF_3$ wherein said alkyl and cycloalkyl are optionally substituted with one to three groups selected from halo, OR, $CF_3$, or CN;
Each $R^a$ is independently H, $C_1$-$C_6$ alkyl, $C_3$-$C_{10}$ cycloalkyl, or $CF_3$ wherein said alkyl, cycloalkyl and aryl are optionally substituted with one to three groups selected from halo, OR, $CF_3$, or CN;
Each $R^b$ is independently H, $C_1$-$C_6$ alkyl, $C_3$-$C_{10}$ cycloalkyl, $CF_3$, or aryl, wherein said alkyl, cycloalkyl and aryl are optionally substituted with one to three groups selected from halo, OR, $CF_3$, or CN;
$R^2$ is triazolyl, oxadiazolyl, imidazolyl, thiazolyl, pyrazolyl, isoxazolyl, thiadiazolyl or oxazolyl, where triazolyl, oxadiazolyl, imidazolyl, thiazolyl, pyrazolyl, isoxazolyl, thiadiazolyl or oxazolyl is optionally substituted with one to two groups from $R^5$;
$R^4$ is H, $C_1$-$C_6$ alkyl, aryl, or $C_3$-$C_{10}$ cycloalkyl, where said alkyl, aryl, or cycloalkyl is optionally substituted with one to four groups selected from halo or OR;
Each $R^5$ is independently OR, $(CR^c_2)_{0-3}$—$CF_3$, $C_1$-$C_6$ alkyl, $(CR^c_2)_{0-3}$—$C_3$-$C_{10}$ cycloalkyl, $(CR^c_2)_{0-3}$-aryl, $(CR^c_2)_{0-3}$-heteroaryl, or $(CR^c_2)_{0-3}$-halo, where said alkyl, cycloalkyl, aryl or heteroaryl is optionally substituted with one to three groups selected from aryl, heteroaryl, heterocyclyl, OR, halo, $CF_3$ or $NH_2$;
Each $R^c$ is independently H, $C_1$-$C_6$ alkyl, or $C_3$-$C_{10}$ cycloalkyl, wherein said alkyl and cycloalkyl are optionally substituted with one to three groups selected from halo, OR, $CF_3$, or CN;
m is 0, 1, 2 or 3; and
p is 0, 1, 2 or 3.
In another embodiment of the compounds of Formula I,
Each $R^a$ is independently H or $C_1$-$C_6$ alkyl wherein said alkyl is optionally substituted with one to three groups selected from halo, OR, $CF_3$, or CN;
$R^2$ is triazolyl, oxadiazolyl, imidazolyl or oxazolyl, where triazolyl, oxadiazolyl, imidazolyl or oxazolyl is optionally substituted with one to two groups from $R^5$;
$R^4$ is aryl or $C_3$-$C_{10}$ cycloalkyl, where said aryl or cycloalkyl is optionally substituted with one to four groups selected from halo or OR;
Each $R^5$ is independently OR, $C_1$-$C_6$ alkyl, $(CR_2)_{0-3}$—$C_3$-$C_{10}$ cycloalkyl, $(CR_2)_{0-3}$-aryl, $(CR_2)_{0-3}$-heteroaryl, or $(CR_2)_{0-3}$-halo, where said alkyl, cycloalkyl, aryl or heteroaryl is optionally substituted with one to three groups selected from aryl, heteroaryl, or heterocyclyl;
m is 0 or 1;
p is 0, 1 or 2;
and all other variables are as previously defined in Formula I.

In a further embodiment, the invention is directed to compounds of Formula I having structural Formula II:

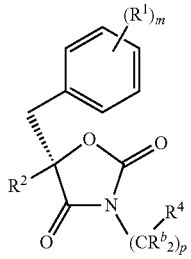

II or a pharmaceutically acceptable salt thereof, wherein

Each $R^1$ is independently halo, $CF_3$, $C_1$-$C_6$ alkyl, $C_3$-$C_{10}$ cycloalkyl, or OR, wherein said alkyl and cycloalkyl are optionally substituted with one to three groups selected from halo, OR, $CF_3$, or CN;

Each R is independently H, $C_1$-$C_6$ alkyl, $C_3$-$C_{10}$ cycloalkyl, or $CF_3$ wherein said alkyl and cycloalkyl are optionally substituted with one to three groups selected from halo, OH, $C_1$-$C_6$ alkoxy, $CF_3$, or CN;

Each $R^b$ is independently H or $C_1$-$C_6$ alkyl, wherein said alkyl is optionally substituted with one to three groups selected from halo, OR, $CF_3$, or CN;

Each $R^c$ is independently H, $C_1$-$C_6$ alkyl, or $C_3$-$C_{10}$ cycloalkyl, wherein said alkyl and cycloalkyl are optionally substituted with one to three groups selected from halo, OR, $CF_3$, or CN;

$R^2$ is triazolyl, oxadiazolyl, imidazolyl or oxazolyl, where triazolyl, oxadiazolyl, imidazolyl or oxazolyl is optionally substituted with one to two groups from $R^5$;

$R^4$ is $C_1$-$C_6$ alkyl, aryl, or $C_3$-$C_{10}$ cycloalkyl, where said alkyl, aryl, or cycloalkyl is optionally substituted with one to four groups selected from halo or OR;

Each $R^5$ is independently $(CR^c{}_2)_{0-3}$—$CF_3$, $C_1$-$C_6$ alkyl, $(CR^c{}_2)_{0-3}$—$C_3$-$C_{10}$ cycloalkyl, $(CR^c{}_2)_{0-3}$-aryl, $(CR^c{}_2)_{0-3}$-heteroaryl, or $(CR^c{}_2)_{0-3}$-halo, where said alkyl, cycloalkyl, aryl or heteroaryl is optionally substituted with one to three groups selected from aryl, heteroaryl, heterocyclyl, OR, halo, $CF_3$ or $NH_2$;

m is 0 or 1; and p is 1 or 2.

In another embodiment of Formula II,

Each $R^b$ is independently H or $C_1$-$C_6$ alkyl;

$R^4$ is aryl, or $C_3$-$C_{10}$ cycloalkyl, where said aryl, or cycloalkyl is optionally substituted with one to four groups selected from halo or OR;

Each $R^5$ is independently $(CR^c{}_2)_{0-3}$—$C_3$-$C_{10}$ cycloalkyl, $(CR^c{}_2)_{0-3}$-aryl, or $(CR^c{}_2)_{0-3}$-heteroaryl, where said alkyl, cycloalkyl, aryl or heteroaryl is optionally substituted with one to three groups selected from aryl, heteroaryl, heterocyclyl, OR, halo, $CF_3$ or $NH_2$;

p is 1;

and all other variables are as previously defined in Formula II.

In an embodiment, a compound which is

| Compound Number | IUPAC Name |
|---|---|
| 1 | 5-Benzyl-5-[5-(3,5-dimethoxyphenyl)-4H-1,2,4-triazol-3-yl]-3-[(1R)-1-(4-fluorophenyl)ethyl]-1,3-oxazolidine-2,4-dione |
| 2 | (5R)-5-Benzyl-5-[5-(3,5-dimethoxybenzyl)-1,3,4-oxadiazol-2-yl]-3-[(1R)-1-phenylethyl]-1,3-oxazolidine-2,4-dione |
| 3 | (5R)-5-Benzyl-5-(5-benzyl-1,3,4-oxadiazol-2-yl)-3-[(1R)-1-phenylethyl]-1,3-oxazolidine-2,4-dione |
| 4 | (5R)-5-Benzyl-5-[5-(3,5-dimethoxyphenyl)-1,3,4-oxadiazol-2-yl]-3-[(1R)-1-phenylethyl]-1,3-oxazolidine-2,4-dione |
| 5 | (5R)-5-Benzyl-5-[5-(1-phenylcyclopropyl)-1,3,4-oxadiazol-2-yl]-3-[(1R)-1-phenylethyl]-1,3-oxazolidine-2,4-dione |
| 6 | (5R)-5-Benzyl-3-[(1R)-1-phenylethyl]-5-(3-phenyl-1,2,4-oxadiazol-5-yl)-1,3-oxazolidine-2,4-dione |
| 7 | (5R)-5-Benzyl-3-[(1R)-1-phenylethyl]-5-(5-pyridin-4-yl-1,3,4-oxadiazol-2-yl)-1,3-oxazolidine-2,4-dione |
| 8 | (5R)-5-Benzyl-5-[5-(4,6-dimethoxypyrimidin-2-yl)-1,3,4-oxadiazol-2-yl]-3-[(1R)-1-phenylethyl]-1,3-oxazolidine-2,4-dione |
| 9 | (5R)-5-Benzyl-5-{5-[1-(3,5-difluorophenyl)cyclopropyl]-1,3,4-oxadiazol-2-yl}-3-[(1R)-1-phenylethyl]-1,3-oxazolidine-2,4-dione |
| 10 | (5R)-5-[5-(3-Amino-5-methoxyphenyl)-1,3,4-oxadiazol-2-yl]-5-benzyl-3-[(1R)-1-phenylethyl]-1,3-oxazolidine-2,4-dione |
| 11 | (5R)-5-Benzyl-3-[(1R)-1-phenylethyl]-5-[5-(2,2,2-trifluoroethyl)-1,3,4-oxadiazol-2-yl]-1,3-oxazolidine-2,4-dione |
| 12 | (5R)-5-Benzyl-3-[(1R)-1-phenylethyl]-5-{5-[1-(trifluoromethyl)cyclopropyl]-1,3,4-oxadiazol-2-yl}-1,3-oxazolidine-2,4-dione |
| 13 | (5R)-5-Benzyl-5-[5-(cyclopropylmethyl)-1,3,4-oxadiazol-2-yl]-3-[(1R)-1-phenylethyl]-1,3-oxazolidine-2,4-dione |
| 14 | (5R)-5-Benzyl-3-[(1R)-1-phenylethyl]-5-[5-(1-pyridin-4-ylcyclopropyl)-1,3,4-oxadiazol-2-yl]-1,3-oxazolidine-2,4-dione |
| 15 | (5R)-5-Benzyl-5-[4-(3,5-dimethoxyphenyl)-1H-imidazol-2-yl]-3-[(1R)-1-phenylethyl]-1,3-oxazolidine-2,4-dione |
| 16 | (5R)-5-Benzyl-3-[(1R)-1-phenylethyl]-5-(5-phenyl-1H-imidazol-2-yl)-1,3-oxazolidine-2,4-dione |
| 17 | (5R)-5-Benzyl-5-(5-benzyl-1H-imidazol-2-yl)-3-[(1R)-1-phenylethyl]-1,3-oxazolidine-2,4-dione |
| 18 | (5R)-5-Benzyl-3-[(1R)-1-phenylethyl]-5-(4-phenyl-1,3-oxazol-2-yl)-1,3-oxazolidine-2,4-dione |
| 19 | (5R)-5-Benzyl-3-[(1R)-1-phenylethyl]-5-(5-phenyl-1,3-oxazol-2-yl)-1,3-oxazolidine-2,4-dione |

-continued

| Compound Number | IUPAC Name |
| --- | --- |
| 20 | (5R)-5-Benzyl-5-(5-benzyl-1,3-oxazol-2-yl)-3-[(1R)-1-phenylethyl]-1,3-oxazolidine-2,4-dione |
| 21 | (5R)-5-Benzyl-3-[(1R)-1-phenylethyl]-5-(3-phenyl-1H-1,2,4-triazol-5-yl)-1,3-oxazolidine-2,4-dione |
| 22 | (5R)-5-Benzyl-5-[5-(3,5-dimethoxyphenyl)-1,3,4-oxadiazol-2-yl]-3-[(1R)-1-phenylethyl]imidazolidine-2,4-dione | or a pharmaceutically acceptable salt thereof.

In a further embodiment, a compound which is

| Compound Number | IUPAC Name |
| --- | --- |
| 1 | 5-Benzyl-5-[5-(3,5-dimethoxyphenyl)-4H-1,2,4-triazol-3-yl]-3-[(1R)-1-(4-fluorophenyl)ethyl]-1,3-oxazolidine-2,4-dione |
| 2 | (5R)-5-Benzyl-5-[5-(3,5-dimethoxybenzyl)-1,3,4-oxadiazol-2-yl]-3-[(1R)-1-phenylethyl]-1,3-oxazolidine-2,4-dione |
| 3 | (5R)-5-Benzyl-5-(5-benzyl-1,3,4-oxadiazol-2-yl)-3-[(1R)-1-phenylethyl]-1,3-oxazolidine-2,4-dione |
| 4 | (5R)-5-Benzyl-5-[5-(3,5-dimethoxypheny)-1,3,4-oxadiazol-2-yl]-3-[(1R)-1-phenylethyl]-1,3-oxazolidine-2,4-dione |
| 5 | (5R)-5-Benzyl-5-[5-(1-phenylcyclopropyl)-1,3,4-oxadiazol-2-yl]-3-[(1R)-1-phenylethyl]-1,3-oxazolidine-2,4-dione |
| 8 | (5R)-5-Benzyl-5-[5-(4,6-dimethoxypyrimidin-2-yl)-1,3,4-oxadiazol-2-yl]-3-[(1R)-1-phenylethyl]-1,3-oxazolidine-2,4-dione |
| 13 | (5R)-5-Benzyl-5-[5-(cyclopropylmethyl)-1,3,4-oxadiazol-2-yl]-3-[(1R)-1-phenylethyl]-1,3-oxazolidine-2,4-dione |
| 15 | (5R)-5-Benzyl-5-[4-(3,5-dimethoxyphenyl)-1H-imidazol-2-yl]-3-[(1R)-1-phenylethyl]-1,3-oxazolidine-2,4-dione |
| 22 | (5R)-5-Benzyl-5-[5-(3,5-dimethoxyphenyl)-1,3,4-oxadiazol-2-yl]-3-[(1R)-1-phenylethyl]imidazolidine-2,4-dione | or a pharmaceutically acceptable salt thereof.

As used herein except where noted, "alkyl" is intended to include both branched- and straight-chain saturated aliphatic hydrocarbon groups having the specified number of carbon atoms. The term "cycloalkyl" means carbocycles containing no heteroatoms. Examples of cycloalkyl include cyclopropyl, cyclobutyl, cyclopentyl, cyclohexyl, cycloheptyl, decahydronaphthyl and the like. Commonly used abbreviations for alkyl groups are used throughout the specification, e.g. methyl may be represented by conventional abbreviations including "Me" or $CH_3$ or a symbol that is an extended bond without defined terminal group, e.g.

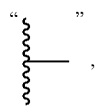

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. If no number is specified, 1-10 carbon atoms are intended for linear or branched alkyl groups. The phrase "$C_{1-6}$ alkyl, wherein the alkyl group may be unsubstituted or substituted with 1-3 fluorine atoms" refers to alkyl groups having 0, 1, 2 or 3 fluorine atoms attached to one or more carbon atoms. The group "$CF_3$," for example, is a methyl group having three fluorine atoms attached the same carbon atom.

As used herein, "$C_{1-6}$ alkoxy" refers to an alkyl group bonded to an oxygen. For example, $C_1$ alkoxy is methoxy group ($-OCH_3$), $C_2$ alkoxy is an ethoxy group ($-OCH_2CH_3$) and the like.

"Aryl" unless otherwise indicated, means mono- and bicyclic aromatic rings containing 6-12 carbon atoms. Examples of aryl include, but are not limited to, phenyl, naphthyl, indenyl and the like. "Aryl" also includes monocyclic rings fused to an aryl group. Examples include dihydroindenyl, tetrahydronaphthalenyl, indanyl and the like. In an embodiment, the preferred aryl is phenyl.

"Heteroaryl" unless otherwise indicated, means a mono- or bicyclic aromatic ring or ring system having 5 to 10 atoms and containing at least one heteroatom selected from O, S and N. Examples include, but are not limited to, pyrrolyl, isoxazolyl, isothiazolyl, pyrazolyl, pyridyl, pyridinyl, oxazolyl, oxadiazolyl, thiadiazolyl, thiazolyl, imidazolyl, triazolyl, tetrazolyl, furanyl, triazinyl, thienyl, pyrimidyl, pyrimidinyl, pyridazinyl, pyrazinyl, and the like. Heteroaryl also includes aromatic heterocyclic groups fused to heterocycles that are non-aromatic or partially aromatic, and aromatic heterocyclic groups fused to cycloalkyl rings. Additional examples of heteroaryls include, but are not limited to, indazolyl, thienopyrazolyl, imidazopyridazinyl, pyrazolopyrazolyl, pyrazolopyridinyl, imidazopyridinyl and imidazothiazolyl. Heteroaryl also includes such groups in charged form, e.g., pyridinium. In an embodiment, heteroaryl is oxadiazolyl, pyrazolyl, oxazolyl, pyridinyl and imidazolyl "Heterocyclyl", unless otherwise indicated, means a 4-, 5- or 6-membered monocyclic saturated ring containing at least one heteroatom selected from N, S and O, in which the point of attachment may be carbon or nitrogen. Examples of "heterocyclyl" include, but are not limited to, azetidinyl, pyrrolidinyl, piperidinyl, piperazinyl, morpholinyl, oxazolidinyl, imidazolidinyl, 2,3-dihydrofuro(2,3-b)pyridyl, benzoxazinyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). Heterocyclyl moreover includes such moieties in charged form, e.g., piperidinium. In an embodiment, heterocyclyl is pyrrolidinyl, piperidinyl, piperazinyl, morpholinyl and oxazolidinyl.

"Halogen (or halo)" unless otherwise indicated, includes fluorine (fluoro), chlorine (chloro), bromine (bromo) and iodine (iodo). In one embodiment, halo is fluorine or chlorine.

By "oxo" is meant the functional group "=O" which is an oxygen atom connected to the molecule via a double bond, such as, for example, (1) "C=(O)", that is a carbonyl group; (2) "S=(O)", that is, a sulfoxide group; and (3) "N=(O)", that is, an N-oxide group, such as pyridyl-N-oxide.

Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

Reference to the compounds of structural Formula I includes the compounds of other generic structural Formulae that fall within the scope of Formula I, including but not limited to Formula II.

When any variable (e.g., R, $R^a$, $R^1$, etc.) occurs more than one time in any constituent or in Formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

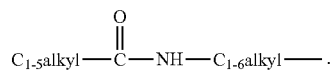

In choosing compounds of the present invention, one of ordinary skill in the art will recognize that the various substituents, i.e. $R^a$, $R^b$, $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Where a substituent or variable has multiple definitions, it is understood that the substituent or variable is defined as being selected from the group consisting of the indicated definitions.

Optical Isomers—Diastereoisomers—Geometric Isomers—Tautomers—Atropisomers:

Compounds of structural Formula I may contain one or more asymmetric centers and can thus occur as racemates and racemic mixtures, single enantiomers, diastereoisomeric mixtures and individual diastereoisomers. The present invention is meant to comprehend all such isomeric forms of the compounds of structural Formula I.

Compounds of structural Formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer or isomers of a compound of the general structural Formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural Formula I. For example, different isotopic forms of hydrogen (H) include protium ($^1$H) and deuterium ($^2$H, also denoted as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates. Thus, the present invention covers isotopically-enriched compounds, including deuterated compounds.

The present invention includes all stereoisomeric forms of the compounds of the Formula I. Centers of asymmetry that are present in the compounds of Formula I can all independently of one another have S configuration or R configuration. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism, the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the Formula I or at the stage of an intermediate during the synthesis. The present invention also includes all tautomeric forms of the compounds of Formula I.

The present invention includes all atropisomer forms of the compounds of Formula I. Atropisomers are stereoisomers resulting from hindered rotation about single bonds where the steric strain barrier to rotation is high enough to allow for the isolation of the conformers. Atropisomers display axial chirality. Separation of atropisomers is possibly by chiral resolution methods such as selective crystallization.

Salts:

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and β-aminoacyl, can be employed. Included are those esters and acyl groups known in the art for modifying the solubility or hydrolysis characteristics for use as sustained-release or prodrug formulations.

Solvates and the hydrates of the compounds of structural Formula I are included in the present invention as well.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

As appropriate, the following embodiments may apply to structural Formulae I and/or II.

In an embodiment, $R^1$ is independently halo, $C_1$-$C_6$ alkyl, or OR, wherein said alkyl is optionally substituted with one to three groups selected from halo, OR, $CF_3$, or CN. In a further embodiment, $R^1$ is independently halo or $C_1$-$C_6$ alkyl. In another embodiment, $R^1$ is independently halo.

In an embodiment, each $R^a$ is independently H or $C_1$-$C_6$ alkyl, wherein said alkyl is optionally substituted with one to three groups selected from $C_1$-$C_6$ alkyl, halo, OR, $CF_3$, or CN. In another embodiment, each $R^a$ is H.

In an embodiment, each $R^b$ is independently H, $C_1$-$C_6$ alkyl, or $C_3$-$C_{10}$ cycloalkyl, wherein said alkyl and cycloalkyl are optionally substituted with one to three groups selected from halo, OR, $CF_3$, or CN. In another embodiment, each $R^b$ is independently H or $C_1$-$C_6$ alkyl, wherein said alkyl is optionally substituted with one to three groups selected from halo, OR, $CF_3$, or CN. In a further embodiment, each $R^b$ is independently H or $C_1$-$C_6$ alkyl.

In an embodiment, $R^2$ is triazolyl, oxadiazolyl, imidazolyl or oxazolyl, where triazolyl, oxadiazolyl, imidazolyl or oxazolyl is optionally substituted with one to two groups from $R^5$.

In an embodiment, $R^4$ is $C_1$-$C_6$ alkyl, aryl, or $C_3$-$C_{10}$ cycloalkyl, where said alkyl, aryl, or cycloalkyl is optionally substituted with one to four groups selected from halo or OR.

In another embodiment, $R^4$ is aryl or $C_3$-$C_{10}$ cycloalkyl, where said aryl, or cycloalkyl is optionally substituted with one to four groups selected from halo or OR. In further embodiment, $R^4$ is aryl, where said aryl is optionally substituted with one to four groups selected from halo or OR. In further embodiment, $R^4$ is phenyl, where said aryl is optionally substituted with one to two groups selected from halo or OR.

In an embodiment, $R^5$ is independently $C_1$-$C_6$ alkyl, $(CR^c_2)_{0-3}$—$C_3$-$C_0$ cycloalkyl, $(CR^c_2)_{0-3}$-aryl, or $(CR^c_2)_{0-3}$-heteroaryl, where said alkyl, cycloalkyl, aryl, or heteroaryl is optionally substituted with one to three aryl, heteroaryl, heterocyclyl, OR, halo, $CF_3$ or $NH_2$ groups. In another embodiment, $R^5$ is independently $(CR^c_2)_{0-3}$—$C_3$-$C_{10}$ cycloalkyl, $(CR^c_2)_{0-3}$-aryl, or $(CR^c_2)_{0-3}$-heteroaryl, where said cycloalkyl, aryl or heteroaryl is optionally substituted with one to three aryl, heteroaryl, heterocyclyl, OR, halo, $CF_3$ or $NH_2$ groups. In further embodiment, $R^5$ is independently $(CR^c_2)_{0-3}$—$C_3$-$C_0$ cycloalkyl, $(CR^c_2)_{0-3}$-aryl, or $(CR^c_2)_{0-3}$-heteroaryl, where said cycloalkyl, aryl or heteroaryl is optionally substituted with one to three OR, aryl, heteroaryl, heterocyclyl, or halo groups.

In an embodiment, m is 0, 1 or 2. In a further embodiment, m is 0 or 1.

In an embodiment, p is 1, 2 or 3. In a further embodiment, p is 1.

The present invention also relates to processes for the preparation of the compounds of Formula I which are described in the following and by which the compounds of the invention are obtainable.

The compounds of the Formula I according to the invention competitively antagonize the aldosterone receptor (MR) and they therefore might be useful agents for the therapy of disorders related to increased aldosterone levels. The ability for the compounds of Formula I to antagonize MR can be examined, for example, in the activity assay described below.

One aspect of the invention that is of interest relates to a compound in accordance with Formula I or a pharmaceutically acceptable salt thereof which might be useful in a method of treatment of the human or animal body by therapy.

Another aspect of the invention that is of interest relates to a compound in accordance with Formula I or a pharmaceutically acceptable salt thereof which might be useful as an anti-hypertensive agent in a human or animal.

Another aspect of the invention that is of interest is a possible method of treating cardiovascular disease, heart failure, hypertension, atherosclerosis, primary hyperaldosteronism or a related condition in a human patient in need of such treatment comprising administering a therapeutically effective amount of a compound of Formula I or a pharmaceutically acceptable salt thereof.

Another aspect of the invention that is of interest relates to a possible method of treating metabolic syndrome in a mammal in need of such treatment, comprising administering a therapeutically effective amount of a compound of Formula I or a pharmaceutically acceptable salt thereof.

Another aspect of the invention that is of interest relates to a possible method of treating a physiological or pathologic disease, selected from including Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels in a human patient in need of such treatment comprising administering to the patient a therapeutically effective amount of a compound of Formula I or a pharmaceutically acceptable salt thereof.

Another aspect of the invention that is of interest is a possible method of treating renal failure in a human patient in need of such treatment comprising administering a therapeutically effective amount of a compound of Formula I or a pharmaceutically acceptable salt thereof.

Another aspect of the invention that is of interest is a possible method of treating hypertension, including, but not limited to, essential hypertension, resistant hypertension, systolic hypertension, pulmonary arterial hypertension, and the like.

Additionally, another aspect of the invention is a possible method of treating hypertension in an obese animal or human.

Additionally, another aspect of the invention is a possible method of treating hypertension in a diabetic animal or human.

Another aspect of the present invention is the possible use of the compounds of Formula I and their pharmaceutically acceptable salts in the prevention or prophylaxis of one or more disease states associated with inhibiting the MR in a mammal by administering an effective amount of a compound of Formula I or a pharmaceutically acceptable salt to a mammal in need thereof.

The compounds of the Formula I and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment (prevention) to prevent or reduce the risk of said disease or medical condition.

A subject of the present invention therefore also are the compounds of the Formula I and their pharmaceutically acceptable salts for use as pharmaceuticals, their use for antagonizing mineralocorticoid receptors and in particular their use in the therapy and prophylaxis of the abovementioned syndromes as well as their potential use for preparing medicaments for these purposes.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing" or "prevention" as used herein refer to administering a compound of Formula I or its pharmaceutically acceptable salt before the onset of clinical symptoms. As an example, the dosage a patient receives can be selected so as to achieve the desired reduction in blood pressure; the dosage a patient receives may also be titrated over time in order to reach a target blood pressure. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hypertension, and a prophylactically effective amount, e.g., for prevention of myocardial infarction.

Furthermore, a subject of the present invention are pharmaceutical preparations (or pharmaceutical compositions) which comprise as active component an effective dose of at least one compound of the Formula I and/or a pharmaceutically acceptable salt thereof and a customary pharmaceutically acceptable carrier, i.e., one or more pharmaceutically acceptable carrier substances and/or additives.

Thus, subjects of the invention are, for example, said compound and its pharmaceutically acceptable salts for use as a pharmaceutical, pharmaceutical preparations which comprise as an active component a therapeutically effective dose of said compound and/or a pharmaceutically acceptable salt thereof and a customary pharmaceutically acceptable carrier, and the uses of said compound and/or a pharmaceutically acceptable salt thereof in the therapy or prophylaxis of the abovementioned syndromes as well as their use for preparing medicaments for these purposes.

The pharmaceutical compositions according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of the Formula I and/or its pharmaceutically acceptable salts in the pharmaceutical preparations normally is from 0.2 to 700 mg, preferably from 1 to 500 mg, per dose, but depending on the type of the pharmaceutical preparation it can also be higher. The pharmaceutical preparations usually comprise 0.5 to 90 percent by weight of the compounds of the Formula I and/or their pharmaceutically acceptable salts. The preparation of the pharmaceutical preparations can be carried out in a manner known per se. For this purpose, one or more compounds of the Formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the Formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of the Formula I to be administered and/or of a pharmaceutically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the Formula I. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compounds of the Formula I bind to the mineralocorticoid receptor and antagonize the biological effects of aldosterone and cortisol. On account of this property, apart from use as pharmaceutically active compounds in human medicine and veterinary medicine, they can also be employed as a scientific tool or as aid for biochemical investigations in which such an effect on the mineralocorticoid receptor is intended, and also for diagnostic purposes, for example in the in vitro diagnosis of cell samples or tissue samples. The compounds of the Formula I and salts thereof can furthermore be employed, as already mentioned above, as intermediates for the preparation of other pharmaceutically active compounds.

The above-mentioned compounds are also of use in combination with other pharmacologically active compounds. Additional active compounds that may be used in combination with the compounds of the instant invention, either co-administered or in a fixed combination, include, but are not limited to the following pharmaceutically acceptable salts, metabolites, solvates, prodrugs or polymorphs thereof: angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan, valsartan, candesartan, olmesartan, telmesartan), neutral endopeptidase inhibitors (e.g., enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide, chlorthalidone, furosemide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., niacin, HMG Co-A reductase inhibitors), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, LY-818, and compounds disclosed in WO02/08188, WO2004/020408, and WO2004/020409.

(b) biguanides, such as metformin and phenformin;

(c) protein tyrosine phosphatase-1B (PTP-1B) inhibitors;

(d) dipeptidyl peptidase-IV (DPP-4) inhibitors, such as sitagliptin, saxagliptin, vildagliptin, and alogliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, pitavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARα agonists, such as fenofibric acid derivatives (gemfibrozil, clofibrate, fenofibrate and bezafibrate), (v) cholesterol absorption inhibitors, such as ezetimibe, (vi) acyl CoA:cholesterol acyltransferase (ACAT) inhibitors, such as avasimibe, (vii) CETP inhibitors, such as torcetrapib, anacetrapib, and dalcetrapib, and (viii) phenolic antioxidants, such as probucol;

(i) PPARα/γ dual agonists, such as muraglitazar, tesaglitazar, farglitazar, and JT-501;

(j) PPARδ agonists, such as those disclosed in WO97/28149;

(k) anti-obesity compounds, such as fenfluramine, dexfenfluramine, phentiramine, subitramine, orlistat, neuropeptide Y Y5 inhibitors, MC4R agonists, cannabinoid receptor 1 (CB-1) antagonists/inverse agonists (e.g., rimonabant and taranabant), and $β_3$ adrenergic receptor agonists;

(l) ileal bile acid transporter inhibitors;

(m) agents intended for use in inflammatory conditions, such as aspirin, non-steroidal anti-inflammatory drugs, glucocorticoids, azulfidine, and cyclooxygenase-2 (Cox-2) selective inhibitors;

(n) glucagon receptor antagonists;

(o) GLP-1;

(p) GIP-1;

(q) GLP-1 analogs and derivatives, such as exendins, (e.g., exenatide and liruglatide), and (r) 11β-hydroxysteroid dehydrogenase-1 (HSD-1) inhibitors.

One or more additional active agents may be administered with the compounds described herein. The additional active agent or agents can be lipid modifying compounds or agents having other pharmaceutical activities, or agents that have both lipid-modifying effects and other pharmaceutical activities. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767), simvastatin (see U.S. Pat. No. 4,444,784), dihydroxy open-acid simvastatin, particularly the ammonium or calcium salts thereof, pravastatin, particularly the sodium salt thereof (see U.S. Pat. No. 4,346,227), fluvastatin particularly the sodium salt thereof (see U.S. Pat. No. 5,354,772), atorvastatin, particularly the calcium salt thereof (see U.S. Pat. No. 5,273,995), pitavastatin also referred to as NK-104 (see PCT international publication number WO 97/23200) and rosuvastatin, also known as CRESTOR®; see U.S. Pat. No. 5,260,440); HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; endothelial lipase inhibitors; bile acid sequestrants; LDL receptor inducers; platelet aggregation inhibitors, for example glycoprotein IIb/IIIa fibrinogen receptor antagonists and aspirin; human peroxisome proliferator activated receptor gamma (PPAR-gamma) agonists including the compounds commonly referred to as glitazones for example pioglitazone and rosiglitazone and, including those compounds included within the structural class known as thiazolidine diones as well as those PPAR-gamma agonists outside the thiazolidine dione structural class; PPAR-alpha agonists such as clofibrate, fenofibrate including micronized fenofibrate, and gemfibrozil; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; diuretics (e.g., chlorthalidone, hydrochlorothiazide), sympatholitics, endothelin antagonists; agents that enhance ABCA1 gene expression; cholesteryl ester transfer protein (CETP) inhibiting compounds, including anacetrapib; 5-lipoxygenase activating protein (FLAP) inhibiting compounds, 5-lipoxygenase (5-LO) inhibiting compounds, farnesoid X receptor (FXR) ligands including both antagonists and agonists; Liver X Receptor (LXR)-alpha ligands, LXR-beta ligands, bisphosphonate compounds such as alendronate sodium; cyclooxygenase-2 inhibitors such as rofecoxib and celecoxib; and compounds that attenuate vascular inflammation.

Throughout the synthetic schemes and examples, abbreviations are used with the following meanings unless otherwise indicated:
ABCA1 is adenosyltriphosphate-binding cassette-family A1
Ac is acetate, acetyl;
ACN is acetonitrile;
aq. is aqueous;
Ar is Aryl;
Bn is benzyl;
Boc is tertbutylcarbamoyl;
Bu is butyl;
CD-FBS is charcoal dextran treated fetal bovine serum
CHO is Chinese hamster ovary
cpm is counts per minute;
° C. is degrees Celsius
δ is chemical shift;
$^cPr$ is cyclopropyl;
DCM is dichloromethane;
DMF is N,N-dimethylformamide;
DMSO is dimethyl sulfoxide;
dppf is 1,1'-bis(diphenylphosphino)ferrocene;
ES-MS is electrospray ion-mass spectroscopy;
Et is ethyl;
F12FBS is F12K media containing fetal bovine serum;
F12K is Kaighn's Modification of Ham's F-12 Medium;
FBS is fetal bovine serum;
FXR is farnesoid X receptor;
HATU is O-(7-azabenzotriazol-1-yl)-N,N,N',N'-tetramethyluronium hexafluorophosphate;
HMG-CoA is 3-hydroxy-3-methyl-glutaryl coenzyme A;
$^1$HNMR is proton nuclear magnetic resonance;
HPLC is high performance liquid chromatography;
Hz is hertz;
i is Iso;
iPr$_2$NEt is diisopropylethyl amine;
IP is the inflection point for a given dose-response titration curve;
kg is kilogram;
LC/MS is Liquid chromatography/Mass Spectroscopy;
LTB$_4$ is leukotriene B$_4$;
LXR is liver X receptor;
M is molar;
Me is methyl;
μg is microgram;
MeCN is acetonitrile;
MeOH is methanol;
MHz is megahertz;
mm is millimeter;
μL is microliter;
mM is milimolar;
MS is mass spectrum, and a mass spectrum obtained by ES-MS may be denoted herein by "ES";
mw is microwave;
m/z is mass to charge ratio;
n is normal;
nm is nanometer;
nPr is n-propyl;
p is para;
PBS is phosphate-buffered saline.
Ph is phenyl;
PPARα is peroxisome proliferator activated receptor alpha;
Pr is propyl;
RP-HPLC is reverse phase high performance liquid chromatography;
rt is room temperature;
sec is secondary;
SFC is supercritical fluid chromatography;
$^tBu$ is tert-butyl;
tert is tertiary;
TFA is trifluoroacetic acid;
THF is tetrahydrofuran;
TMSCHN$_2$ is trimethylsilyldiazomethane;
U is units;
UV is ultraviolet.

SCHEMES

Synthetic methods for preparing the compounds of the present invention are illustrated in the following Schemes and Examples. Starting materials are commercially available or may be made according to procedures known in the art or as illustrated herein.

Reaction schemes 1-7 illustrate the methods employed in the synthesis of the compounds of Formula I. All abbreviations are as defined above unless indicated otherwise. In the Schemes, all substituents are as defined above in Formula I unless indicated otherwise.

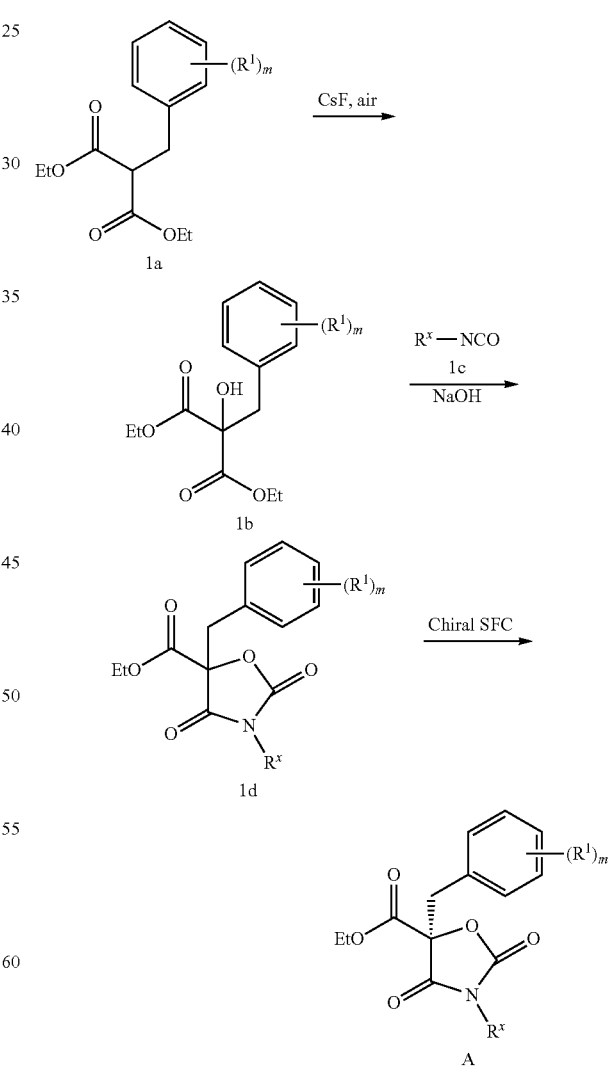

SCHEME 1

As shown in SCHEME 1, diethyl malonate derivative 1a was treated with cesium fluoride and oxidized in the presence of air to afford hydroxy malonate 1b. Treatment of 1b with isocyanate 1c, followed by cyclization yielded oxazolidine dione 1d. Ethyl ester 1d was resolved using a chiral SFC method to afford intermediate A.

SCHEME 2

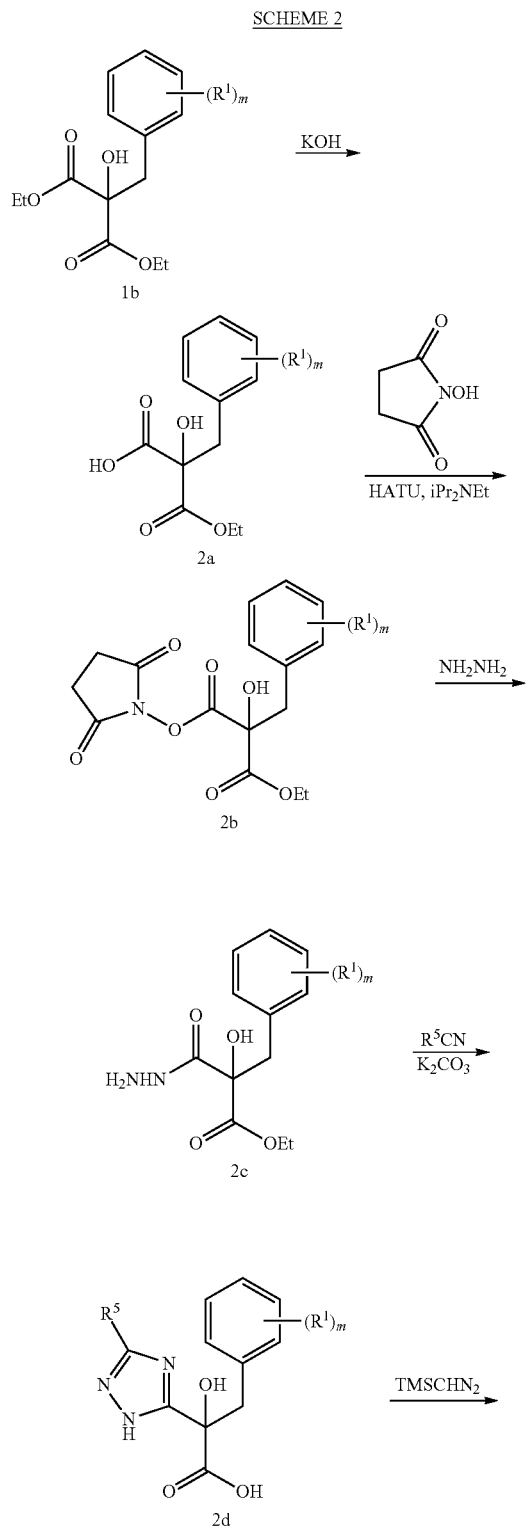

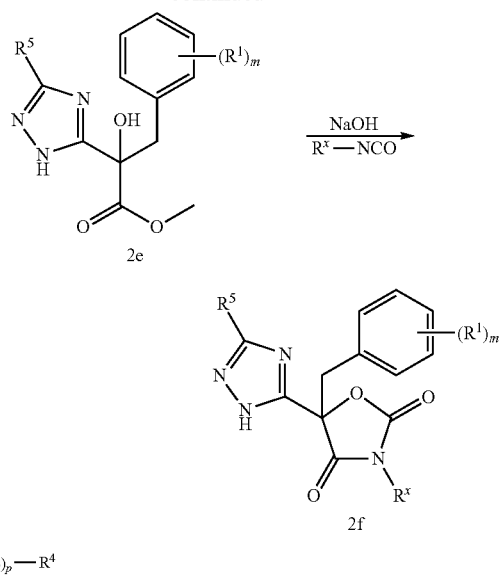

$R^x = (CR^b{}_2)_p$—$R^4$

As shown in SCHEME 2, treatment of ethyl ester 1b with aqueous potassium hydroxide provided carboxylic acid 2a. Acid 2a was treated with N-hydroxysuccinimide to give activated ester 2b, which was then reacted with hydrazine to generate hydrazide 2c. Hydrazide 2c was subsequently condensed with an alkyl nitrile under basic conditions to form 1,2,4-triazole 2d, which was esterafide using trimethylsilyl-diazomethane to give methyl ester 2e. Hydroxy ester 2e was then reacted with an isocyanate, undergoing a tandem intramolecular cyclization to give oxazolidinedione 2f.

SCHEME 3

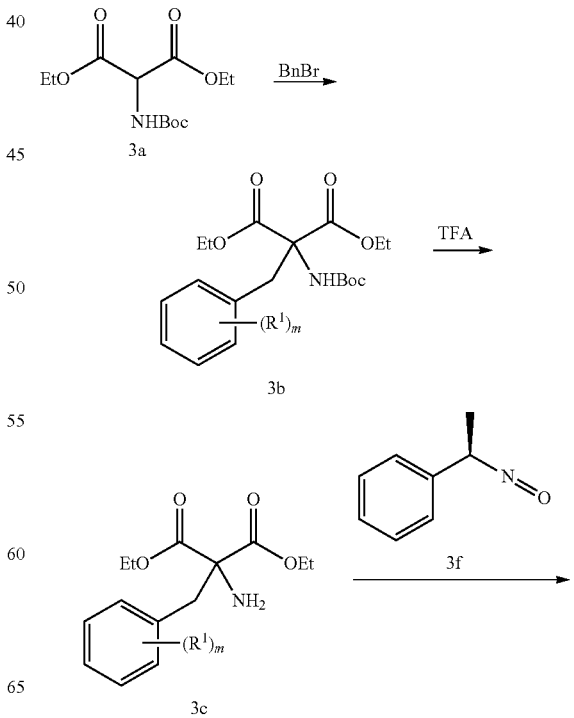

-continued

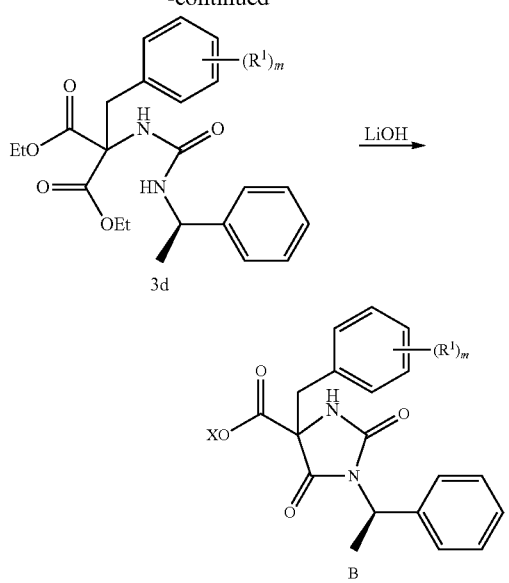

X = H, Li

Intermediates of the formula B are known in the literature or may be conveniently prepared by a variety of methods familiar to those skilled in the art. One common route is illustrated in SCHEME 3. Amino-malonate 3a is treated with benzyl bromide in the presence of base, such as sodium ethoxide, in a suitable solvent, such as ethanol to provide 3b. Removal of the Boc protecting group using acid, such as trifluoroacetic acid affords amine 3c. Amine 3c is reacted with an appropriate isocyanate, such as 3f, in a suitable solvent, such as N,N-dimethylormamide, in the presence of base, such as diisopropylethylamine to afford urea 3d. Urea 3d is converted to Intermediate B by treatment of 3d with base, such as aqueous lithium hydroxide, in a suitable solvent, such as methanol, tetrahydrofuran or a combination of both.

SCHEME 4

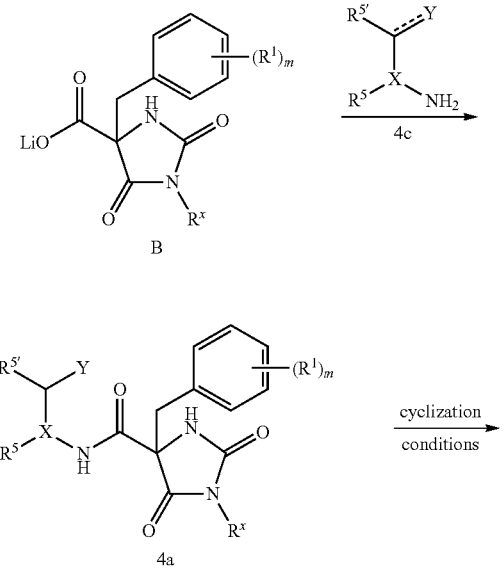

-continued

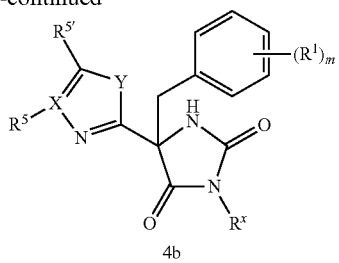

X = C, N
Y = N, O
$R^x = (CR^b{}_2)_p$—$R^4$
$R^5$ and $R^{5'}$ can be the same or different, as defined in $R^5$ of Formulae I/II As illustrated in SCHEME 4, compounds of the formula 4b can be prepared by first treatment of Intermediate B with substituted amines, such as 4c by a variety of methods familiar to those skilled in the art to afford amide 4a. Amide 4a can be cyclized under a variety of methods familiar to those skilled in the art, to provide heterocycle 4b.

SCHEME 5

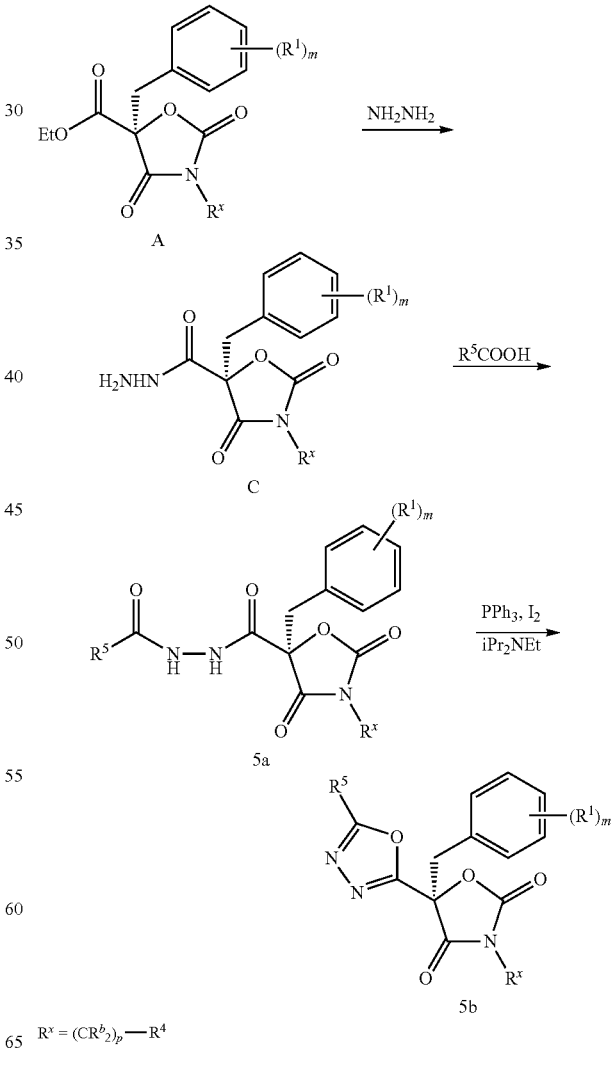

$R^x = (CR^b{}_2)_p$—$R^4$

As illustrated in SCHEME 5, the compounds of the present invention with structural formula 5c may be prepared from Intermediate A by first addition of hydrazine in a suitable solvent such as methanol to afford Intermediate C. Treatment of C with a suitable carboxylic acid, carboxylic acid chloride, or carboxylic acid anhydride in the presence of a suitable coupling reagent such as O-(7-azabensotriazol-1yl)-N,N,N', N'-tetramethyluronium hexafluorophosphate and a suitable base such as N,N-diisopropylethylamine provides 5a. Compound 5a can be cyclized to oxadiazole 5b via appropriate methods such as treatment with triphenylphosphine in the presence of iodine and a suitable base such as N,N-diisopropylethylamine.

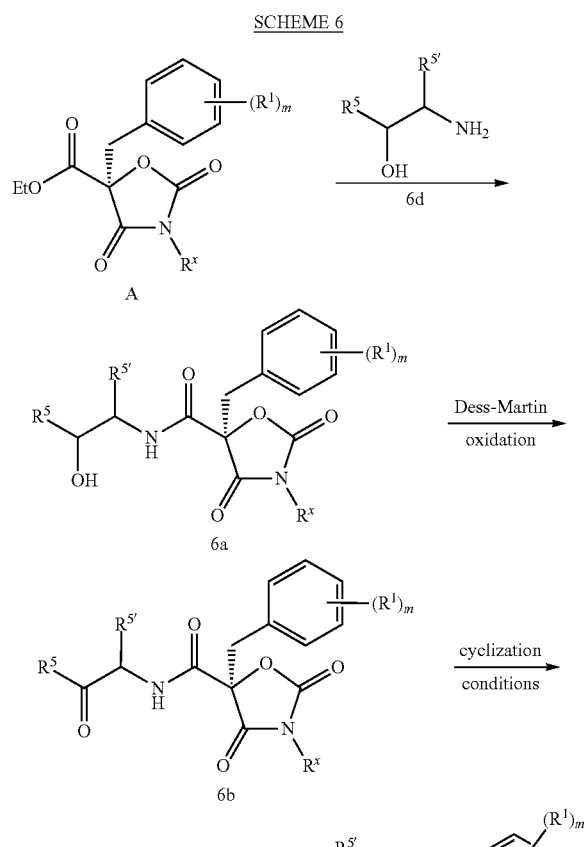

As illustrated in SCHEME 6, the compounds of the present invention with structural formula 6c may be prepared from Intermediate A by first heating in the presence of amino alcohol 6d in a suitable solvent such as ethanol to provide 6a. Oxidation of alcohol 6a with an oxidant such as Dess-Martin periodinane, in a suitable solvent such dichloromethane provides 6b. Reaction of 6b under appropriate cyclization conditions familiar to those skilled in the art, provides heterocycle 6c.

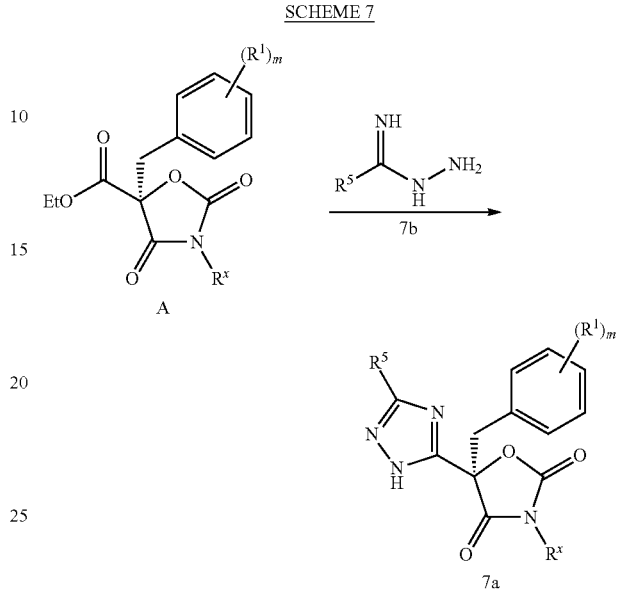

Compound 7a can be prepared as described in SCHEME 7, by heating Intermediate A with 7b in a suitable solvent, such as 2-methoxylethanol.

The following examples are provided so that the invention might be more fully understood. Unless otherwise indicated, the starting materials are commercially available. They should not be construed as limiting the invention in any way.

REPRESENTATIVE EXAMPLES

The following examples are provided to more fully illustrate the present invention, and shall not be construed as limiting the scope in any manner. Unless stated otherwise:

All operations were carried out at room or ambient temperature (rt), that is, at a temperature in the range 18-25° C.;

Reactions are generally done using commercially available anhydrous solvents under an inert atmosphere, either nitrogen or argon;

Microwave reactions were done using a Biotage Initiator™ or CEM Explorer® system;

Evaporation of solvent was carried out using a rotary evaporator under reduced pressure (4.5-30 mmHg) with a bath temperature of up to 50° C.;

The course of reactions was followed by thin layer chromatography (TLC) and/or tandem high performance liquid chromatography (HPLC) followed by electron spray mass spectroscopy (MS), herein termed LCMS, and any reaction times are given for illustration only;

The structure of all final compounds was assured by at least one of the following techniques: MS or proton nuclear magnetic resonance (1H NMR) spectrometry, and the purity was assured by at least one of the following techniques: TLC or HPLC;

¹H NMR spectra were recorded on either a Varian Unity or a Varian Inova instrument at 400, 500 or 600 MHz using the indicated solvent; when line-listed, NMR data is in the form of delta values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad; etc.; MS data were recorded on a Waters Micromass unit, interfaced with a Hewlett-Packard (Agilent 1100) HPLC instrument, and operating on MassLynx/OpenLynx software; electrospray ionization was used with positive (ES+) or negative ion (ES−) detection; and diode array detection.

Purification of compounds by preparative reverse phase HPLC was performed on a Gilson system using a YMC-Pack Pro C18 column (150×20 mm i.d.) eluting at 20 mL/min with a water/acetonitrile (0.1% TFA) gradient (5% acetonitrile to 95% acetonitrile) or on a Shimadzu system using a Sunfire Prep C18 OBD 5 μM column (100×30 mm i.d.) eluting at 50 mL/min with a water/acetonitrile (0.1% TFA) gradient;

Purification of compounds by preparative thin layer chromatography (PTLC) was conducted on 20×20 cm glass plates coated with silica gel, commercially available from Analtech; or E. Merck.

Flash column chromatography was carried out on a glass silica gel column using Kieselgel 60, 0.063-0.200 mm (SiO₂), or on a Biotage SiO₂ cartridge system using the Biotage Horizon and Biotage SP-1 systems; or a Teledyne Isco SiO₂ cartridge using the CombiFlashRf system; Chemical symbols have their usual meanings, and the following abbreviations have also been used: h (hours), min (minutes), d (days), v (volume), w (weight), b.p. (boiling point), m.p. (melting point), L (litre(s)), mL (millilitres), g (gram(s)), mg (milligrams(s)), mol (moles), mmol (millimoles), eq or equiv (equivalent(s)), IC50 (molar concentration which results in 50% of maximum possible inhibition), EC50 (molar concentration which results in 50% of maximum possible efficacy), μM (micromolar), nM (nanomolar).

In the Tables in the following Examples, compounds having mass spectral data were synthetically prepared.

Intermediate A

Ethyl (5R)-benzyl-2,4-dioxo-3-[(1R)-1-phenylethyl]-1,3-oxazolidine-5-carboxylate

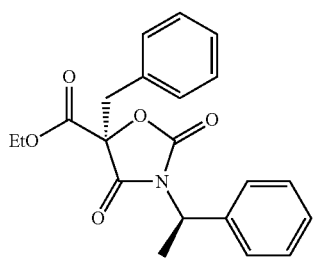 [SMILES: CCOC(=O)[C@@]1(Cc2ccccc2)OC(=O)N([C@H](C)c2ccccc2)C1=O]

Step A: Diethyl benzyl(hydroxy)propanedioate

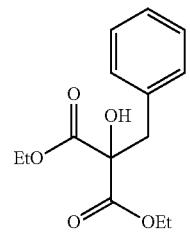 [SMILES: CCOC(=O)C(O)(Cc1ccccc1)C(=O)OCC]

A mixture of diethyl benzylpropanedioate (41 g) and CsF (49.8 g) in 90 mL of DMF was heated at 40° C. with vigorous air bubbling for 3 days. The resulting mixture was diluted with ethyl acetate (800 mL) and washed with water (3×1 L). The organic layer was concentrated and then purified by Biotage silica gel column chromatography (5-20% ethyl acetate in hexanes) to give the title product as a colorless oil. ¹H NMR (300 MHz, CDCl₃) δ: 7.22-7.26 (m, 5H), 4.23 (q, J=7.2 Hz, 4H), 3.80 (br, 1H), 3.35 (s, 2H), 1.26 (t, J=7.2 Hz, 6H).

Step B: Ethyl 5-benzyl-2,4-dioxo-3-[(1R)-1-phenylethyl]-1,3-oxazolidine-5-carboxylate

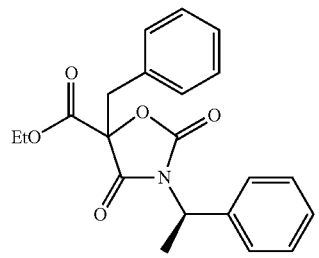 [SMILES: CCOC(=O)C1(Cc2ccccc2)OC(=O)N([C@H](C)c2ccccc2)C1=O]

To a mixture of NaOH (25 g) and 15.7 g of activated molecular sieves in 1159 mL of THF at 0° C. was added a 1159 mL THF solution of diethyl benzyl(hydroxy)propanedioate (153 g). After 5 min, to this mixture was added [(1R)-1-isocyanatoethyl]benzene (118 g). The mixture was stirred at 0° C. for 30 min and then warmed to ambient temperature and stirred for 4 h. The reaction mixture was directly purified using a Biotage silica gel chromatography system (5-30% ethyl acetate in hexanes) to give the title compound.

Step C: Ethyl (5R)-benzyl-2,4-dioxo-3-[(1R)-1-phenylethyl]-1,3-oxazolidine-5-carboxylate

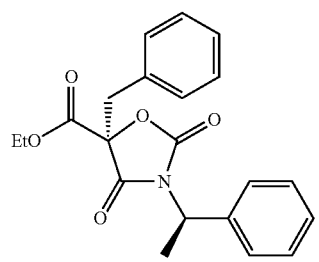

The purification of ethyl 5-benzyl-2,4-dioxo-3-[(1R)-1-phenylethyl]-1,3-oxazolidine-5-carboxylate by chiral SFC following the conditions below provided the title compound as a single diastereomer. ¹H NMR: 400 MHz, CDCl₃) δ: 7.170-7.253 (m, 8H), 6.957-6.980 (m, 2H), 5.018 (q, J=7.2 Hz, 1H), 4.196-4.337 (m, 2H), 3.545 (d, J=14.4 Hz, 1H), 3.401 (d, J=14.4 Hz, 1H), 1.503 (d, J=7.6 Hz, 3H), 1.242 (t, J=7.6 Hz, 3H).

Chiral SFC (Supercritical Fluid Chromatography) Separation conditions:
Instrument: Berger MultiGram™ SFC, Mettler Toledo Co, Ltd.
Column: AD 250 mm×50 mm
Mobile phase: A: Supercritical $CO_2$, B: MeOH, A:B=75:25 at 160 mL/min
Column Temp: 38° C.
Nozzle Pressure: 100 Bar
Nozzle Temp: 60° C.
Evaporator Temp: 20° C.
Trimmer Temp: 25° C.
Wavelength: 220 nm Intermediate B Lithium 4-benzyl-2,5-dioxo-1-[(1R)-1-phenylethyl]imidazolidine-4-carboxylate

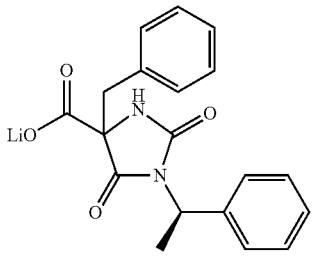

Step A: Diethylbenzyl[(tert-butoxycarbonyl)amino]propanedioate

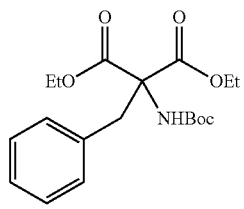 [SMILES: CCOC(=O)C(Cc1ccccc1)(NC(=O)OC(C)(C)C)C(=O)OCC]

To diethyl[(tert-butoxycarbonyl)amino]propanedioate (5.56 mL, 21.79 mmol) in ethanol (30 ml) was added sodium ethoxide (9.76 ml, 26.2 mmol) followed by benzyl bromide (2.59 mL, 21.79 mmol). The mixture was stirred for 6 h, and the solvent was removed in vacuo. Saturated aqueous sodium hydrogen carbonate (50 mL) was added and the mixture was extracted with ethyl acacate (3×50 mL). The combined organic fractions were washed with saturated aqueous brine (1×50 mL), dried with anhydrous sodium sulfate, filtered and the solvent removed in vacuo to afford the title compound as a colorless amorphous solid. LC/MS 366.1 (M+1).

Step B: Diethylamino(benzyl)propanedioate trifluoroacetate

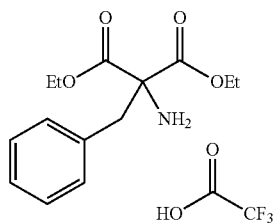

To the product of Step A (7.5 g, 20.52 mmol) in dichloromethane (24 mL) was added trifluoroacetic acid (12 mL, 156 mmol) and the mixture stirred for 1 h. The solvent was removed in vacuo and the oil azeotroped with toluene (2×20 mL) to afford the title compound as a tan amorphous solid. LC/MS 266.1 (M+1).

Step C: Diethylbenzyl({[(1R)-1-phenylethyl]carbamoyl}amino)propanedioate

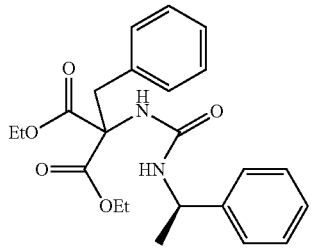 [SMILES: CCOC(=O)C(Cc1ccccc1)(NC(=O)N[C@H](C)c1ccccc1)C(=O)OCC]

To the product from Step B (7.79 g, 20.54 mmol) in N,N-dimethylormamide (100 mL) was added diisopropylethylamine (10.76 mL, 61.6 mmol) at 0° C. the mixture was stirred for 5 min then (R)-(+)-1-phenylethyl isocyanate (3.76 mL, 26.7 mmol) was added dropwise. The mixture was warmed to ambient temperature over 30 min and stirred for 16 h. Water (150 mL) was added and a white solid crashed out, the mixture was filtered and the solid washed with water. The solid was diluted in ethyl acetate (250 mL) and half saturated aqueous sodium hydrogen carbonate (200 mL) was added and the mixture was extracted with ethyl acetate (4×50 mL). The combined organic fractions were washed with brine (saturated, 1×100 mL), dried with anhydrous sodium sulfate, filtered and the solvent removed in vacuo to afford the title compound as a colorless amorphous solid. LC/MS 413.1 (M+1).

Step D: Lithium 4-benzyl-2,5-dioxo-1-[(1R)-1-phenylethyl]imidazolidine-4-carboxylate

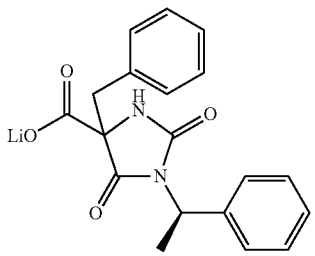

To a solution of the product from Step C (7.8 g, 18.91 mmol) in tetrahydrofuran (60 mL) and methanol (20.00 mL) was added a 1 M lithium hydroxide solution (19.86 mL, 19.86 mmol) and the mixture stirred for 30 min. The solvent was removed in vacuo and the residue azeotroped with toluene (3×25 mL) to afford the title compound as a colorless amorphous solid. LC/MS 339.1 (M+1).

Intermediate C

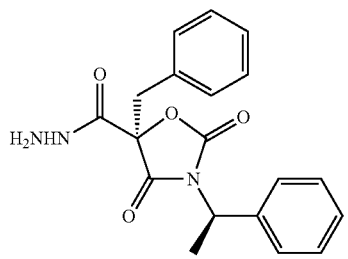

(5S)-5-Benzyl-2,4-dioxo-3-[(1R)-1-phenylethyl]-1,3-oxazolidine-5-carbohydrazide

To a slurry of Intermediate A (4 g, 10.89 mmol) in methanol (18 mL) was added anhydrous hydrazine (0.376 mL, 11.98 mmol) and the mixture was sonicated for 1 h. The solvent was removed in vacuo to afford the crude title compound as a colorless solid. LC/MS 354.1 (M+1).

Example 1

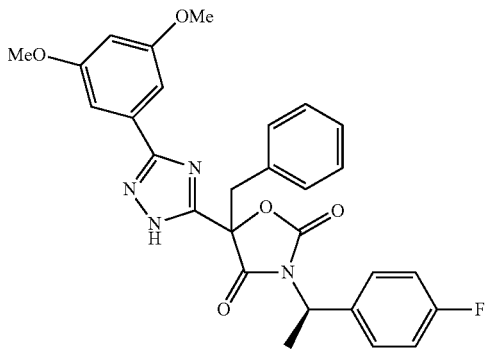 [SMILES: COc1cc(OC)cc(-c2n[nH]c(C3(Cc4ccccc4)OC(=O)N([C@H](C)c4ccc(F)cc4)C3=O)n2)c1]

5-Benzyl-5-[5-(3,5-dimethoxyphenyl)-4H-1,2,4-triazol-3-yl]-3-[(1R)-1-(4-fluorophenyl)ethyl]-1,3-oxazolidine-2,4-dione (Compound 1)

Step A: Ethyl 2-benzyl-3-hydrazinyl-2-hydroxy-3-oxopropanoate

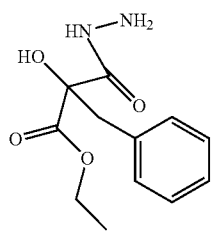

A mixture of 2-benzyl-3-ethoxy-2-hydroxy-3-oxopropanoic acid (250 mg), HATU (479 mg), diisopropylethyl amine (149 mg) and N-hydroxysuccinamide (145 mg) in 4 mL of DMF was stirred at ambient temperature for 1.5 h. The mixture was diluted with ethyl acetate, washed with water. The organic layer was dried with magnesium sulfate and concentrated to give the desired product ethyl 2-benzyl-3-hydrazinyl-2-hydroxy-3-oxopropanoate (352 mg), which was directly used for the next step. To ethyl 2-benzyl-3-hydrazinyl-2-hydroxy-3-oxopropanoate (352 mg) in DCM (5 mL) was added hydrazine (anhydrous, 101 mg) at ambient temperature. Instantaneously the solution turned cloudy and after 15 min the solvent was removed in vacuo to afford the crude title compound as an amorphous solid. LC/MS 275.2 (M+23).

Step B: Methyl 2-[5-(3,5-dimethoxyphenyl)-4H-1,2,4-triazol-3-yl]-2-hydroxy-3-phenylpropanoate

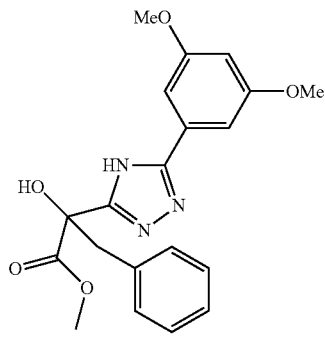 [SMILES: COC(=O)C(O)(Cc1ccccc1)c1nnc(-c2cc(OC)cc(OC)c2)[nH]1]

To the mixture of ethyl 2-benzyl-3-hydrazinyl-2-hydroxy-3-oxopropanoate (40 mg), 3,5-dimethoxybenzonitrile (55 mg) and $K_2CO_3$ (44 mg) in 2 mL of n-butanol was heated at 160° C. for 1.5 h. The mixture was then diluted with ethyl acetate and water. The aqueous layer was washed with ethyl acetate and then acidified until pH=1. The mixture was then extracted with 30% isopropanol in chloroform. The organic layer was dried with magnesium sulfate and concentrated to give the crude acid, which was then dissolved in methanol. To the resulting solution was added $TMSCHN_2$ (0.3 mL, 2 M in Et2O) at rt. After 30 min, the mixture was concentrated and purified by Gilson RP-HPLC (30-100% ACN/water/0.05% TFA) to give methyl 2-[5-(3,5-dimethoxyphenyl)-4H-1,2,4-triazol-3-yl]-2-hydroxy-3-phenylpropanoate as a yellow oil.

Step C: 5-Benzyl-5-[5-(3,5-dimethoxyphenyl)-4H-1,2,4-triazol-3-yl]-3-[(1R)-1-(4-fluorophenyl)ethyl]-1,3-oxazolidine-2,4-dione

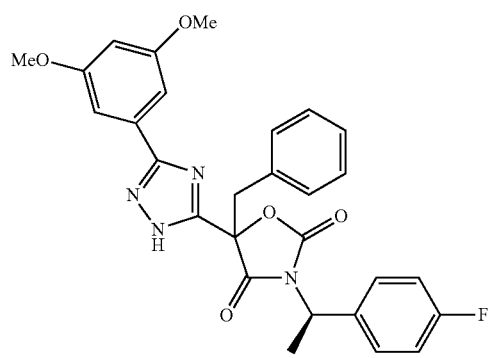 [SMILES: COc1cc(OC)cc(-c2n[nH]c(C3(Cc4ccccc4)OC(=O)N([C@H](C)c4ccc(F)cc4)C3=O)n2)c1]

To a solution of methyl 2-[5-(3,5-dimethoxyphenyl)-4H-1,2,4-triazol-3-yl]-2-hydroxy-3-phenylpropanoate (7 mg) in 1 mL of THF was added NaOH (4 mg) and (R)-1-fluoro-4-(1-isocyanatoethyl)benzene (15 mg). The resulting mixture was stirred at ambient temperature overnight. The resulting mixture was diluted with ethyl acetate, and then quenched with water. The organic layer was concentrated and purified by reverse phase HPLC (YMC Pro-C18 column, gradient elution, 30% to 100% acetonitrile/water with 0.1% TFA) to give the title compound. LC/MS 517.2 (M+1). $IC_{50}$ value=C rating.

Example 2

(5R)-5-Benzyl-5-[5-(3,5-dimethoxybenzyl)-1,3,4-oxadiazol-2-yl]-3-[(1R)-1-phenylethyl]-1,3-oxazolidine-2,4-dione (Compound 2)

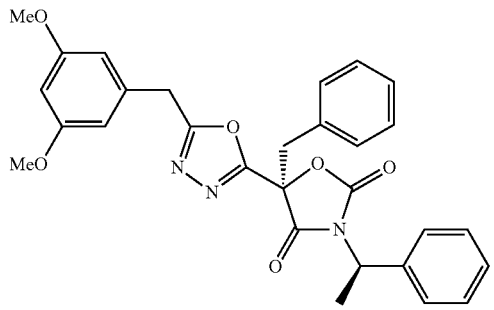 [SMILES: COc1cc(Cc2nnc([C@@]3(Cc4ccccc4)OC(=O)N([C@H](C)c4ccccc4)C3=O)o2)cc(OC)c1]

Step A: (5S)-5-Benzyl-N-[(3,5-dimethoxyphenyl)acetyl]-2,4-dioxo-3-[(1R)-1-phenylethyl]-1,3-oxazolidine-5-carbohydrazide

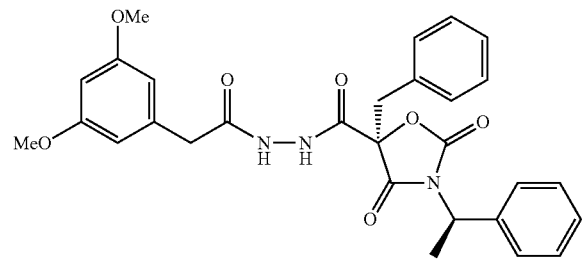 [SMILES: COc1cc(CC(=O)NNC(=O)[C@@]2(Cc3ccccc3)OC(=O)N([C@H](C)c3ccccc3)C2=O)cc(OC)c1]

To Intermediate C (75 mg, 0.212 mmol) in dichloromethane (2 ml), was added (3,5-dimethoxyphenyl)acetic acid (51.0 mg, 0.255 mmol), N,N-diisopropylethylamine (0.074 mL, 0.424 mmol, and O-(7-azabensotriazol-1yl)-N,N,N',N'-tetramethyluronium hexafluorophosphate (105 mg, 0.276 mmol) sequentially. The mixture was stirred at ambient temperature for 1.5 h and saturated aqueous sodium hydrogen carbonate (5 mL) added. The layers were separated and the aqueous phase extracted with dichloromethane (3×5 mL). The combined organic phases were washed with saturated aqueous brine (1×5 mL), dried with anhydrous sodium sulfate, filtered and the solvent removed in vacuo. The yellow oil was purified by column chromatography (silica gel 40 g column) eluting with ethyl acetate/hexane (gradient from 0% to 70%) to give the title compound as a colorless amorphous solid. LC/MS 532.1 (M+1).

Step B: (5R)-5-Benzyl-5-[5-(3,5-dimethoxybenzyl)-1,3,4-oxadiazol-2-yl]-3-[(1R)-1-phenylethyl]-1,3-oxazolidine-2,4-dione

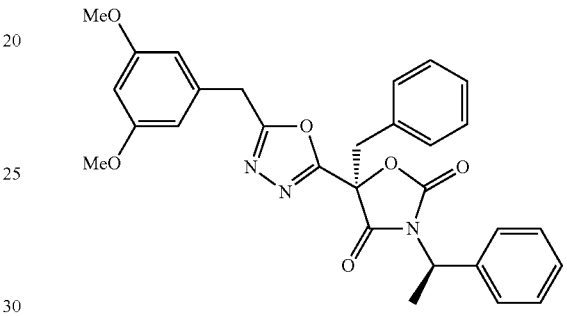

To Iodine (102 mg, 0.400 mmol) in dichloromethane (2 mL) was added triphenylphosphine (108 mg, 0.41 mmol). After 5 min triethylamine (0.112 mL, 0.8 mmol) was added. After 5 min a solution of the product from Step A (53.2 mg, 0.1 mmol) in dichloromethane (2 mL) was added. After stirring at ambient temperature for 1 h, a 1:1 mixture of saturated aqueous sodium hydrogen carbonate and saturated aqueous sodium thiosulfate (5 mL) was added. The biphasic mixture was stirred for 10 min, the layers were separated and the aqueous phase extracted with dichloromethane (3×5 mL). The combined organic phases were washed with saturated aqueous brine (1×5 mL), dried with anhydrous sodium sulfate, filtered and the solvent removed in vacuo. The yellow oil was purified by reverse phase HPLC (YMC Pro-C 18 column, gradient elution, 20% to 100% acetonitrile/water with 0.1% TFA) to afford the title compound as a colorless amorphous solid. LC/MS 514.1 (M+1). IC50 value=A rating.

Following the procedures described above, but using the appropriately substituted carboxylic acid, the compounds in Table 1 below were made.

TABLE 1

| Compound Number | IC$_{50}$ Rating | Structure | IUPAC Name | Exact Mass [M + H]+ |
|---|---|---|---|---|
| 3 | B | 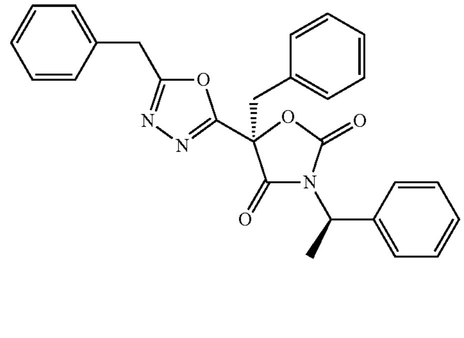 [SMILES: C[C@H](c1ccccc1)N1C(=O)O[C@](Cc2ccccc2)(c2nnc(Cc3ccccc3)o2)C1=O] | (5R)-5-Benzyl-5-(5-benzyl-1,3,4-oxadiazol-2-yl)-3-[(1R)-1-phenylethyl]-1,3-oxazolidine-2,4-dione | 454.1 |

TABLE 1-continued

| Compound Number | IC$_{50}$ Rating | Structure | IUPAC Name | Exact Mass [M + H]+ |
|---|---|---|---|---|
| 4 | A | 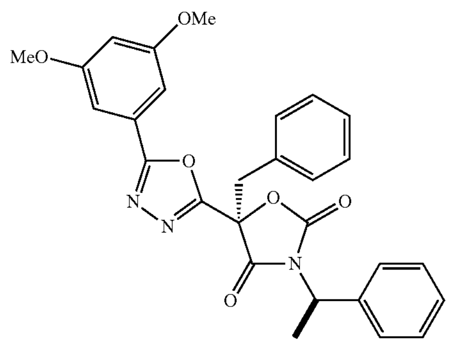 [SMILES: COc1cc(OC)cc(-c2nnc([C@@]3(Cc4ccccc4)OC(=O)N([C@H](C)c4ccccc4)C3=O)o2)c1] | (5R)-5-Benzyl-5-[5-(3,5-dimethoxyphenyl)-1,3,4-oxadiazol-2-yl]-3-[(1R)-1-phenylethyl]-1,3-oxazolidine-2,4-dione | 500.1 |
| 5 | A | 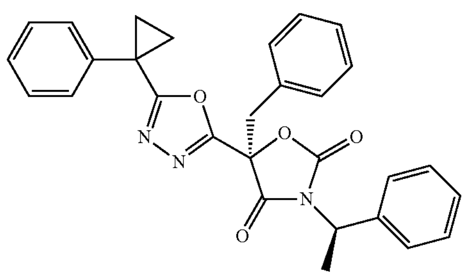 [SMILES: C[C@H](c1ccccc1)N1C(=O)O[C@](Cc2ccccc2)(c2nnc(C3(c4ccccc4)CC3)o2)C1=O] | (5R)-5-Benzyl-5-[5-(1-phenylcyclopropyl)-1,3,4-oxadiazol-2-yl]-3-[(1R)-1-phenylethyl]-1,3-oxazolidine-2,4-dione | 480.1 |
| 6 | B | 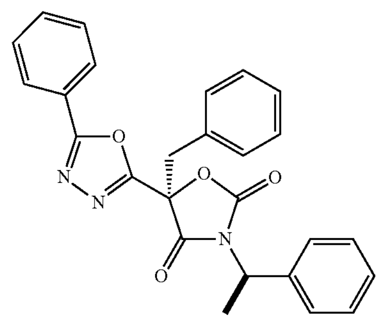 [SMILES: C[C@H](c1ccccc1)N1C(=O)O[C@](Cc2ccccc2)(c2nnc(-c3ccccc3)o2)C1=O] | (5R)-5-Benzyl-3-[(1R)-1-phenylethyl]-5-(3-phenyl-1,2,4-oxadiazol-5-yl)-1,3-oxazolidine-2,4-dione | 440.1 |
| 7 | C | 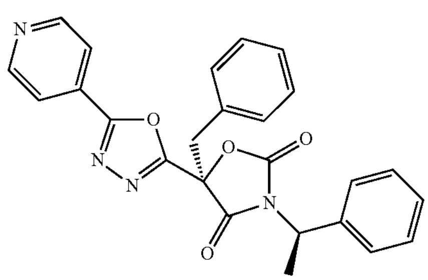 [SMILES: C[C@H](c1ccccc1)N1C(=O)O[C@](Cc2ccccc2)(c2nnc(-c3ccncc3)o2)C1=O] | (5R)-5-Benzyl-3-[(1R)-1-phenylethyl]-5-(5-pyridin-4-yl-1,3,4-oxadiazol-2-yl)-1,3-oxazolidine-2,4-dione | 441.1 |
| 8 | B | 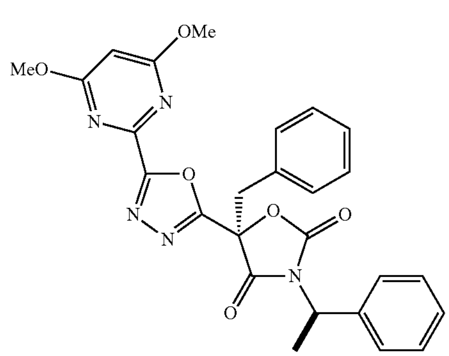 [SMILES: COc1cc(OC)nc(-c2nnc([C@@]3(Cc4ccccc4)OC(=O)N([C@H](C)c4ccccc4)C3=O)o2)n1] | (5R)-5-Benzyl-5-[5-(4,6-dimethoxypyrimidin-2-yl)-1,3,4-oxadiazol-2-yl]-3-[(1R)-1-phenylethyl]-1,3-oxazolidine-2,4-dione | 502.1 |

TABLE 1-continued

| Compound Number | IC$_{50}$ Rating | Structure | IUPAC Name | Exact Mass [M + H]+ |
|---|---|---|---|---|
| 9 | B | 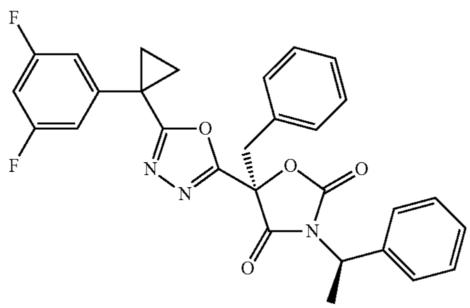 [SMILES: C[C@H](c1ccccc1)N1C(=O)O[C@](Cc2ccccc2)(c2nnc(C3(c4cc(F)cc(F)c4)CC3)o2)C1=O] | (5R)-5-Benzyl-5-{5-[1-(3,5-difluorophenyl)cyclopropyl]-1,3,4-oxadiazol-2-yl}-3-[(1R)-1-phenylethyl]-1,3-oxazolidine-2,4-dione | 516.1 |
| 10 | B | 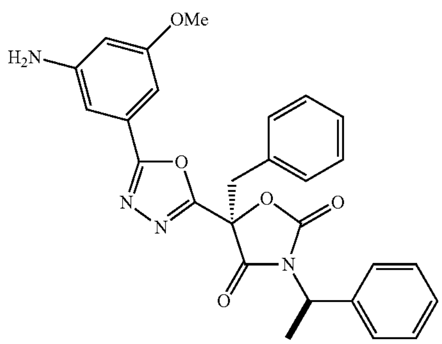 [SMILES: COc1cc(N)cc(-c2nnc([C@@]3(Cc4ccccc4)OC(=O)N([C@H](C)c4ccccc4)C3=O)o2)c1] | (5R)-5-[5-(3-Amino-5-methoxyphenyl)-1,3,4-oxadiazol-2-yl]-5-benzyl-3-[(1R)-1-phenylethyl]-1,3-oxazolidine-2,4-dione | 485.1 |
| 11 | C | 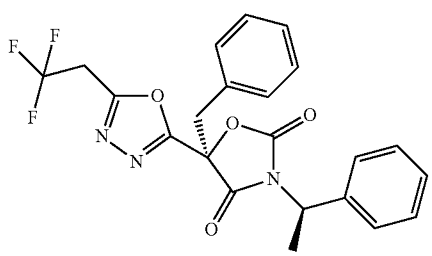 [SMILES: C[C@H](c1ccccc1)N1C(=O)O[C@](Cc2ccccc2)(c2nnc(CC(F)(F)F)o2)C1=O] | (5R)-5-Benzyl-3-[(1R)-1-phenylethyl]-5-[5-(2,2,2-trifluoroethyl)-1,3,4-oxadiazol-2-yl]-1,3-oxazolidine-2,4-dione | 446.1 |
| 12 | C | 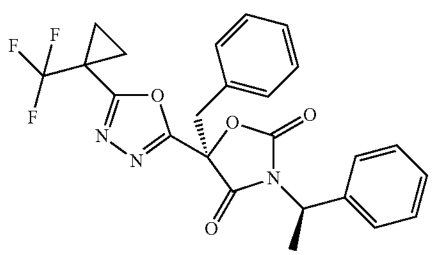 [SMILES: C[C@H](c1ccccc1)N1C(=O)O[C@](Cc2ccccc2)(c2nnc(C3(C(F)(F)F)CC3)o2)C1=O] | (5R)-5-Benzyl-3-[(1R)-1-phenylethyl]-5-{5-[1-(trifluoromethyl)cyclopropyl]-1,3,4-oxadiazol-2-yl}-1,3-oxazolidine-2,4-dione | 472.1 |
| 13 | B | 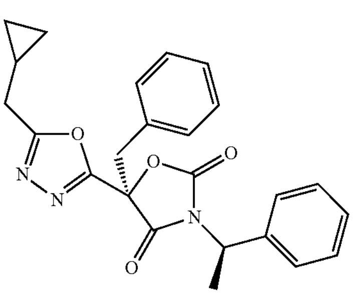 [SMILES: C[C@H](c1ccccc1)N1C(=O)O[C@](Cc2ccccc2)(c2nnc(CC3CC3)o2)C1=O] | (5R)-5-Benzyl-5-[5-(cyclopropylmethyl)-1,3,4-oxadiazol-2-yl]-3-[(1R)-1-phenylethyl]-1,3-oxazolidine-2,4-dione | 418.1 |

TABLE 1-continued

| Compound Number | IC$_{50}$ Rating | Structure | IUPAC Name | Exact Mass [M + H]+ |
|---|---|---|---|---|
| 14 | B | 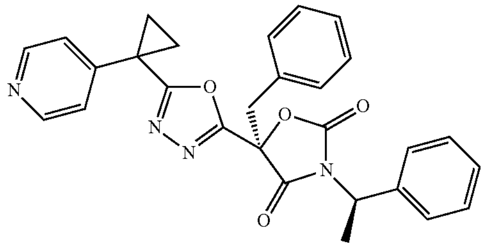 [SMILES: C[C@H](c1ccccc1)N1C(=O)O[C@](Cc2ccccc2)(c2nnc(C3(c4ccncc4)CC3)o2)C1=O] | (5R)-5-Benzyl-3-[(1R)-1-phenylethyl]-5-[5-(1-pyridin-4-ylcyclopropyl)-1,3,4-oxadiazol-2-yl]-1,3-oxazolidine-2,4-dione | 481.1 |

Example 3

(5R)-5-Benzyl-5-[4-(3,5-dimethoxyphenyl)-1H-imidazol-2-yl]-3-[(1R)-1-phenylethyl]-1,3-oxazolidine-2,4-dione (Compound 15)

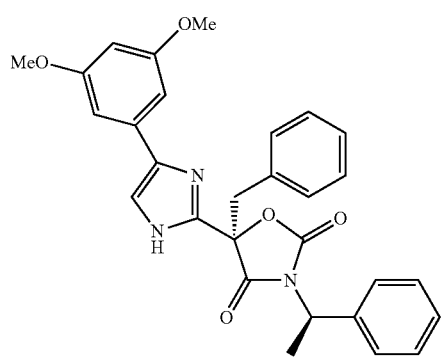 [SMILES: COc1cc(OC)cc(-c2c[nH]c([C@@]3(Cc4ccccc4)OC(=O)N([C@H](C)c4ccccc4)C3=O)n2)c1]

Step A: (5R)-5-Benzyl-N-[2-(3,5-dimethoxyphenyl)-2-hydroxyethyl]-2,4-dioxo-3-[(1R)-1-phenylethyl]-1,3-oxazolidine-5-carboxamide

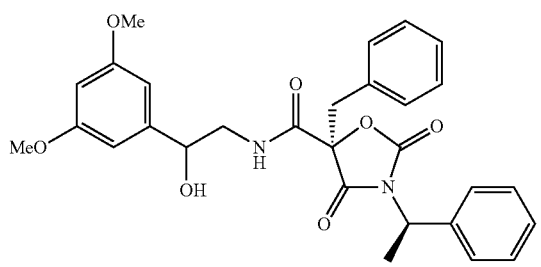 [SMILES: COc1cc(OC)cc(C(O)CNC(=O)[C@@]2(Cc3ccccc3)OC(=O)N([C@H](C)c3ccccc3)C2=O)c1]

To Intermediate A (250 mg, 0.680 mmol) in ethanol (3 mL) was added 2-hydroxy-2-(3,5-dimethoxyphenyl)ethylamine (268 mg, 1.361 mmol) and the mixture was heated at 70° C. for 2 h. The solvent was removed and the residue was purified by column chromatography (silica gel 40 g column) eluting with ethyl acetate/hexane (gradient from 0% to 100%) to give the title compound as a colorless amorphous solid. LC/MS 519.1 (M+1).

Step B: (5R)-5-Benzyl-N-[2-(3,5-dimethoxyphenyl)-2-oxoethyl]-2,4-dioxo-3-[(1R)-1-phenylethyl]-1,3-oxazolidine-5-carboxamide

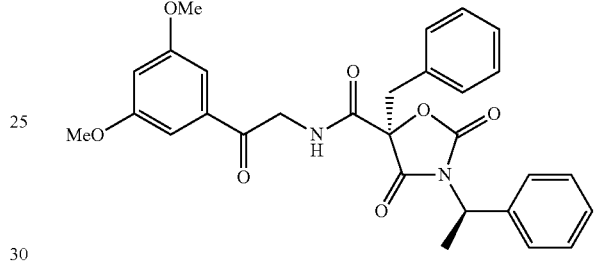

To the product from Step A (310 mg, 0.598 mmol) in dichloromethane (5 mL) was added Dess-Martin periodinane (392 mg, 0.897 mmol) and the mixture was stirred for 30 min. A 1:1 mixture of saturated aqueous sodium bicarbonate and saturated aqueous sodium thiosulfate (20 mL) was added and the mixture was stirred rapidly for 15 min. The layers were separated and the aqueous phase extracted with dichloromethane (3×10 mL). The combined organic phases were washed with saturated aqueous brine (1×15 mL), dried with anhydrous sodium sulfate, filtered and the solvent removed in vacuo, to afford the crude colorless title compound as an amorphous solid. LC/MS 517.1 (M+1).

Step C: (5R)-5-Benzyl-5-[4-(3,5-dimethoxyphenyl)-1H-imidazol-2-yl]-3-[(1R)-1-phenylethyl]-1,3-oxazolidine-2,4-dione

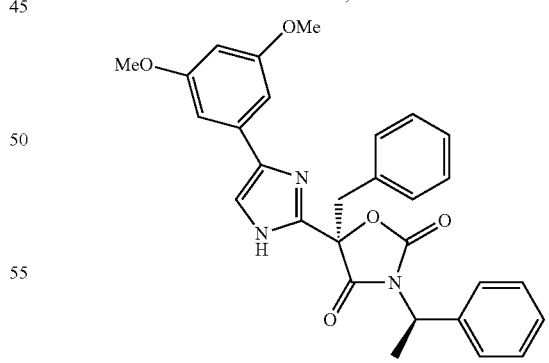

To the product from Step B (40 mg, 0.077 mmol) in acetic acid (1 mL) was added ammonium acetate (179 mg, 2.323 mmol) and the mixture heated at 100° C. for 40 h. The solvent was removed and the yellow oil was purified by reverse phase HPLC(YMC Pro-C 18 column, gradient elution, 20% to 90% acetonitrile/water with 0.1% TFA) to afford the title compound as a colorless amorphous solid. LC/MS 498.1 (M+1). IC$_{50}$ value=B rating Using the procedures described above, the following Examples in the attached Table were made.

TABLE 2

| Compound Number | IC$_{50}$ Rating | Structure | IUPAC Name | Exact Mass [M + H]+ |
|---|---|---|---|---|
| 16 | B | 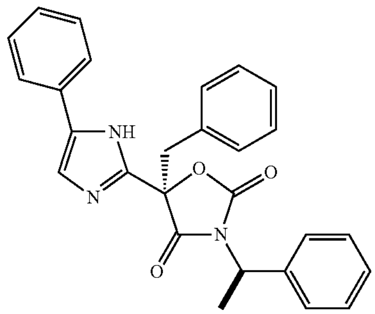 [SMILES: C[C@H](c1ccccc1)N1C(=O)O[C@](Cc2ccccc2)(c2ncc(-c3ccccc3)[nH]2)C1=O] | (5R)-5-Benzyl-3-[(1R)-1-phenylethyl]-5-(5-phenyl-1H-imidazol-2-yl)-1,3-oxazolidine-2,4-dione | 438.1 |
| 17 | B | 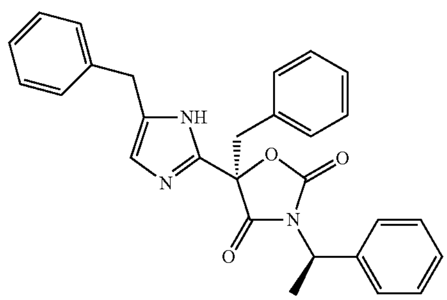 [SMILES: C[C@H](c1ccccc1)N1C(=O)O[C@](Cc2ccccc2)(c2ncc(Cc3ccccc3)[nH]2)C1=O] | (5R)-5-Benzyl-5-(5-benzyl-1H-imidazol-2-yl)-3-[(1R)-1-phenylethyl]-1,3-oxazolidine-2,4-dione | 452.1 |

Example 4

(5R)-5-Benzyl-3-[(1R)-1-phenylethyl]-5-(4-phenyl-1,3-oxazol-2-yl)-1,3-oxazolidine-2,4-dione (Compound 18)

Step A: (5R)-5-Benzyl-N-(2-hydroxy-1-phenylethyl)-2,4-dioxo-3-[(1R)-1-phenylethyl]-1,3-oxazolidine-5-carboxamide

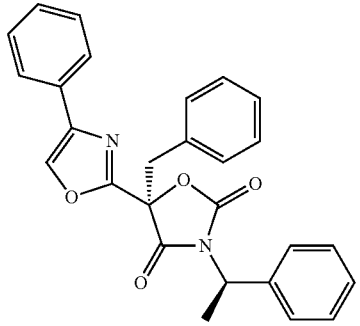 [SMILES: C[C@H](c1ccccc1)N1C(=O)O[C@](Cc2ccccc2)(c2nc(-c3ccccc3)co2)C1=O]

To Intermediate A (200 mg, 0.544 mmol) in ethanol (2 mL) was added 2-phenylglycinol (373 mg, 2.72 mmol) and the mixture was heated at 70° C. for 2 h. The solvent was removed and the residue was purified by column chromatography (silica gel 40 g column) eluting with ethyl acetate/hexane (gradient from 0% to 50%) to give the title compound as a colorless amorphous solid. LC/MS 459.1 (M+1).

Step B: (5R)-5-Benzyl-2,4-dioxo-N-(2-oxo-1-phenylethyl)-3-[(1R)-1-phenylethyl]-1,3-oxazolidine-5-carboxamide

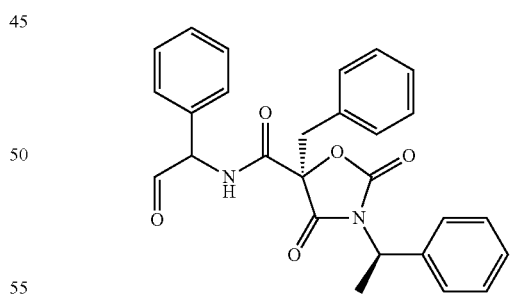

To the product from Step A (250 mg, 0.545 mmol) in dichloromethane (5 mL) was added Dess-Martin periodinane (358 mg, 0.818 mmol) and the mixture was stirred for 30 min. A 1:1 mixture of saturated aqueous sodium bicarbonate and saturated aqueous sodium thiosulfate (20 mL) was added and the mixture was stirred rapidly for 15 min. The layers were separated and the aqueous phase extracted with dichloromethane (3×10 mL). The combined organic phases were washed with saturated aqueous brine (1×15 mL), dried with anhydrous sodium sulfate, filtered and the solvent removed in vacuo, to afford the crude colorless title compound as an amorphous solid. LC/MS 457.1 (M+1).

Step C: (5R)-5-Benzyl-3-[(1R)-1-phenylethyl]-5-(4-phenyl-1,3-oxazol-2-yl)-1,3-oxazolidine-2,4-dione

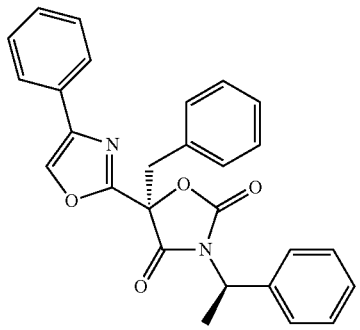 [SMILES: C[C@H](c1ccccc1)N1C(=O)O[C@](Cc2ccccc2)(c2nc(-c3ccccc3)co2)C1=O]

To iodine (111 mg, 0.438 mmol) in dichloromethane (2 mL) was added triphenylphosphine (121 mg, 0.46 mmol). After 5 min triethylamine (0.122 mL, 0.876 mmol) was added. After 5 min a solution of the product from Step B (100 mg, 0.219 mmol) in dichloromethane (2 mL) was added. After stirring at ambient temperature for 1 h, a 1:1 mixture of saturated aqueous sodium hydrogen carbonate and saturated aqueous sodium thiosulfate (5 mL) was added. The biphasic mixture was stirred for 10 min, the layers were separated and the aqueous phase extracted with dichloromethane (3×5 mL). The combined organic phases were washed with saturated aqueous brine (1×5 mL), dried with anhydrous sodium sulfate, filtered and the solvent removed in vacuo. The yellow oil was purified by reverse phase HPLC(YMC Pro-C 18 column, gradient elution, 20% to 100% acetonitrile/water with 0.1% TFA) to afford the title compound as a colorless amorphous solid. LC/MS 439.1 (M+1). IC$_{50}$ value=C rating.

Example 5

(5R)-5-Benzyl-3-[(1R)-1-phenylethyl]-5-(5-phenyl-1,3-oxazol-2-yl)-1,3-oxazolidine-2,4-dione (Compound 19)

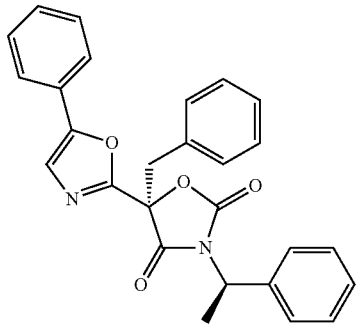 [SMILES: C[C@H](c1ccccc1)N1C(=O)O[C@](Cc2ccccc2)(c2ncc(-c3ccccc3)o2)C1=O]

Step A: (5R)-5-Benzyl-N-(2-hydroxy-2-phenylethyl)-2,4-dioxo-3-[(1R)-1-phenylethyl]-1,3-oxazolidine-5-carboxamide

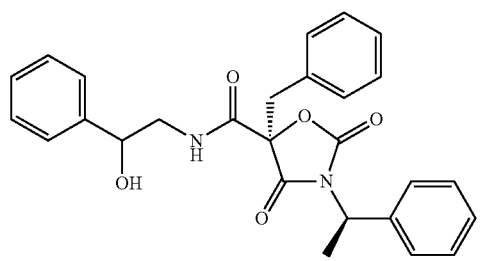 [SMILES: C[C@H](c1ccccc1)N1C(=O)O[C@](Cc2ccccc2)(C(=O)NCC(O)c2ccccc2)C1=O]

To Intermediate A (200 mg, 0.544 mmol) in ethanol (3 mL) was added 2-amino-1-phenylethanol (149 mg, 1.09 mmol) and the mixture was heated at 70° C. for 2 h. The solvent was removed and the residue was purified by column chromatography (silica gel 40 g column) eluting with ethyl acetate/hexane (gradient from 0% to 100%) to give the title compound as a colorless amorphous solid. LC/MS 459.1 (M+1).

Step B: (5R)-5-Benzyl-2,4-dioxo-N-(2-oxo-2-phenylethyl)-3-[(1R)-1-phenylethyl]-1,3-oxazolidine-5-carboxamide

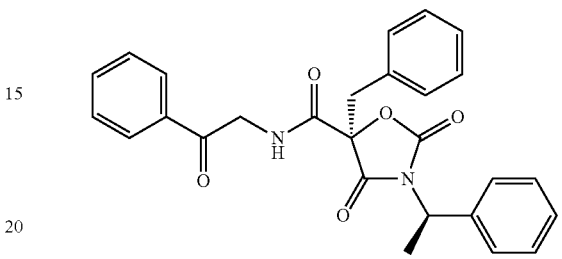

To the product from Step A (100 mg, 0.218 mmol) in dichloromethane (3 mL) was added Dess-Martin periodinane (143 mg, 0.327 mmol) and the mixture was stirred for 30 min. A 1:1 mixture of saturated aqueous sodium bicarbonate and saturated aqueous sodium thiosulfate (10 mL) was added and the mixture was stirred rapidly for 15 min. The layers were separated and the aqueous phase extracted with dichloromethane (3×10 mL). The combined organic phases were washed with saturated aqueous brine (1×15 mL), dried with anhydrous sodium sulfate, filtered and the solvent removed in vacuo, to afford the crude colorless title compound as an amorphous solid. LC/MS 457.1 (M+1).

Step C: (5R)-5-Benzyl-3-[(1R)-1-phenylethyl]-5-(5-phenyl-1,3-oxazol-2-yl)-1,3-oxazolidine-2,4-dione

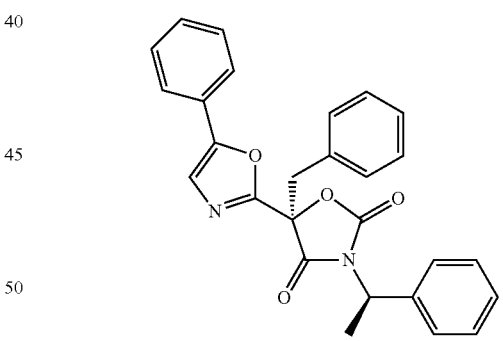

To the product of Step B (40 mg, 0.088 mmol) was added concentrated sulfuric acid (0.5 mL, 9.38 mmol) and the mixture stirred for 16 h. Ice was added followed by saturated aqueous sodium hydrogen carbonate (30 mL) and the mixture was extracted with ethyl acetate (3×10 mL). The combined organic fractions were washed with saturated aqueous brine (1×15 mL), dried with anhydrous sodium sulfate, filtered and the solvent removed in vacuo. The yellow oil was purified by reverse phase HPLC(YMC Pro-C 18 column, gradient elution, 20% to 100% acetonitrile/water with 0.1% TFA) to afford the title compound as a colorless amorphous solid. LC/MS 439.1 (M+1). IC$_{50}$ value=C rating The following Example in the attached Table was made by essentially following the same procedures described above.

TABLE 3

| Compound Number | IC$_{50}$ Rating | Structure | IUPAC Name | Exact Mass [M + H]+ |
|---|---|---|---|---|
| 20 | B | 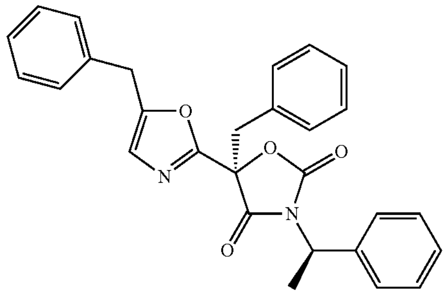 [SMILES: C[C@H](c1ccccc1)N1C(=O)O[C@](Cc2ccccc2)(c2ncc(Cc3ccccc3)o2)C1=O] | (5R)-5-Benzyl-5-(5-benzyl-1,3-oxazol-2-yl)-3-[(1R)-1-phenylethyl]-1,3-oxazolidine-2,4-dione | 453.1 |

Example 6

(5R)-5-Benzyl-3-[(1R)-1-phenylethyl]-5-(3-phenyl-1H-1,2,4-triazol-5-yl)-1,3-oxazolidine-2,4-dione (Compound 21)

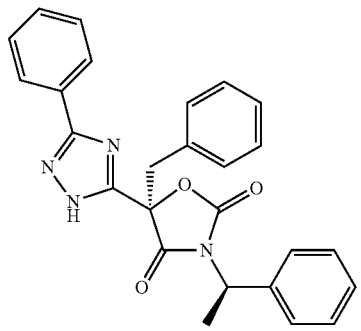 [SMILES: C[C@H](c1ccccc1)N1C(=O)O[C@](Cc2ccccc2)(c2nc(-c3ccccc3)n[nH]2)C1=O]

To Intermediate A (150 mg, 0.408 mmol) in 2-methoxyethanol (2 mL) was added benzenecarboximidohydrazide hydroiodide (107 mg, 0.408 mmol) followed by N,N-diisopropylethylamine (0.071 mL, 0.408 mmol). The mixture was heated at 70° C. for 1 h, and the solvent removed in vacuo. The yellow oil was purified by reverse phase HPLC(YMC Pro-C18 column, gradient elution, 55% to 85% acetonitrile/water with 0.1% TFA) to afford the title compound as a colorless amorphous solid. LC/MS 439.1 (M+1). IC$_{50}$ value=C Rating

Example 7

(5R)-5-Benzyl-5-[5-(3,5-dimethoxyphenyl)-1,3,4-oxadiazol-2-yl]-3-[(1R)-1-phenylethyl]imidazolidine-2,4-dione (Compound 22)

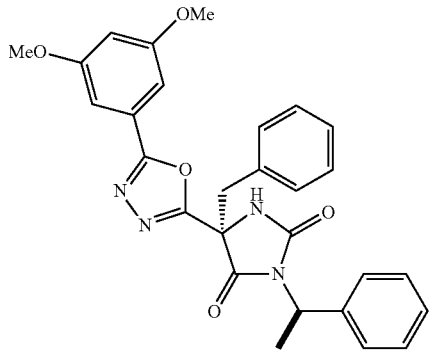 [SMILES: COc1cc(OC)cc(-c2nnc([C@@]3(Cc4ccccc4)NC(=O)N([C@H](C)c4ccccc4)C3=O)o2)c1]

Step A: 4-Benzyl-N'-[(3,5-dimethoxyphenyl)carbonyl]-2,5-dioxo-1-[(1R)-1-phenylethyl]imidazolidine-4-carbohydrazide

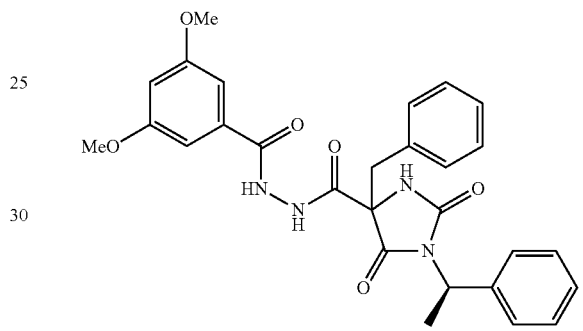

To Intermediate A (200 mg, 0.581 mmol), 3,5-dimethoxybenzhydrazide (125 mg, 0.639 mmol) in N,N-dimethylformamide (2.5 mL) was added N,N-diisopropylethylamine (0.152 mL, 0.871 mmol) and O-(7-azabensotriazol-1yl)-N,N,N',N'-tetramethyluronium hexafluorophosphate (265 mg, 0.697 mmol) sequentially. The reaction mixture was stirred for 16 h, diluted with ethyl acetate (50 mL), washed with water (2×10 mL), saturated aqueous brine (1×10 mL), dried with anhydrous sodium sulfate, filtered and the solvent removed in vacuo. The residue was purified by column chromatography (silica gel 40 g column) eluting with ethyl acetate/hexane (gradient from 0% to 100%) to give the title compound as a colorless amorphous solid. LC/MS 517.1 (M+1).

Step B: (5R)-5-Benzyl-5-[5-(3,5-dimethoxyphenyl)-1,3,4-oxadiazol-2-yl]-3-[(1R)-1-phenylethyl]imidazolidine-2,4-dione

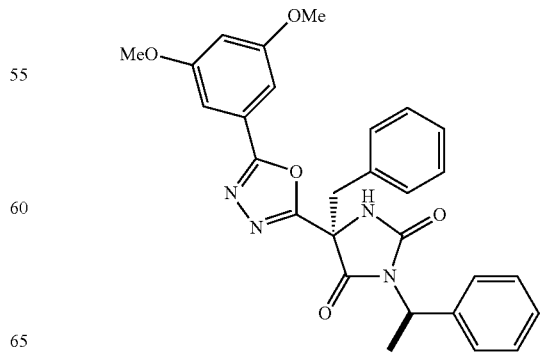

To a stirring solution of iodine (354 mg, 1.394 mmol) in dichloromethane (8 mL) was added triphenylphosphine (375 mg, 1.429 mmol). After 5 min triethylamine (0.389 mL, 2.79 mmol) was added. After 5 min a solution of the product from Step A (180 mg, 0.348 mmol) in dichloromethane (3 mL) was added. After stirring at ambient temperature for 1 h, a 1:1 mixture of saturated aqueous sodium hydrogen carbonate and saturated aqueous sodium thiosulfate (5 mL) was added. The biphasic mixture was stirred for 10 min, the layers were separated and the aqueous phase extracted with dichloromethane (3×5 mL). The combined organic phases were washed with saturated aqueous brine (1×5 mL), dried with anhydrous sodium sulfate, filtered and the solvent removed in vacuo. The residue was purified by column chromatography (silica gel 40 g column) eluting with ethyl acetate/hexane (gradient from 0% to 100%) to give a mixture of diastereomers as a colorless amorphous solid. The isomers were separated via chiral HPLC (ChiralPak AS-H; 40% 2:1 methanol:acetonitrile/carbon dioxide) to afford the first eluting isomer (5R)-5-Benzyl-5-[5-(3,5-dimethoxyphenyl)-1,3,4-oxadiazol-2-yl]-3-[(1R)-1-phenylethyl]imidazolidine-2,4-dione (2.25 minutes) and the second eluting isomer (5S)-5-Benzyl-5-[5-(3,5-dimethoxyphenyl)-1,3,4-oxadiazol-2-yl]-3-[(1R)-1-phenylethyl]imidazolidine-2,4-dione (3.45 minutes) as colorless amorphous solids. LC/MS 499.1 (M+1). $IC_{50}$ value=C rating for the title compound.

Biological Assay

The activity of the compounds of the present invention regarding mineralocorticoid receptor antagonism was evaluated using the following assay.

Assessment of Mr Potency in HMN NH Pro Assay

The human MR NH Pro assay is a commercially available PathHunter™ Protein: Protein interaction assay (DiscoveRx; http://www.discoverx.com/nhrs/prod-nhrs.php) that measures the ability of compounds to antagonize full-length human Mineralocorticoid Receptor (MR) binding to a coactivator peptide. PathHunter™ CHO-K1 cells that overexpress human MR (Cat #93-0456C2, Lot No: 09B0913) were cultured in growth media (F12K w/Glutamine and phenol red (Gibco 11765-047) supplemented with 10% HI FBS (Gibco 16000); 0.25 mg/ml Hygromycin in PBS (Invitrogen 10687-010, 50 mg/ml); 100 I.U./mL and 100 µg/mL Pen/Strep (Gibco 15140-122); 0.6 mg/mL Geneticin).

Compounds were assessed for MR antagonist activity by incubating the cells with a titrating dose of compound in F12K w/Glutamine and phenol red culture media (Invitrogen 11765-047) supplemented with 1% Charcoal/Dextran Treated FBS (Hyclone #SH30068.01) and aldosterone (0.3 nM) for 6 hours at 37° C. Cells were then treated with DiscoveRx detection reagent for 1 hour at room temperature and read using an Envision luminescence plate reader. % activity was measured relative to cells treated with aldosterone alone and $IC_{50}$ values were calculated using ADA software.

1. Growth Media:
F12K w/Glutamine and phenol red (Gibco 11765-047)
10% HI FBS (Gibco 16000)
0.25 mg/ml Hygromycin in PBS (Invitrogen 10687-010, 50 mg/ml)
100 I.U./mL and 100 µg/mL Pen/Strep (Gibco 15140-122)
0.6 mg/mL Geneticin (Gibco 10131, 50 mg/ml)
2. Assay Media:
Fl2K w/Glutamine and phenol red (Invitrogen 11765-047)
1% Charcoal/Dextran Treated FBS (Hyclone #SH30068.01)
3. 3× PathHunter Detection Reagents (Cat #93-0001) (need ~6 ml/plate). Do not freeze and thaw the reagents more than 3 times.
19× PathHunter Cell Assay Buffer
5× Emerald II
1× Galacton Star
4. Control Agonist: Aldosterone: Sigma cat #A9477
Prepare stock solution—10 µM in DMSO kept at −20° C.
for assay, dilute in assay media to 1.8 or 6 nM (6× of final concentration=about 0.3 nM to about 1.0 nM)
5. Cell line: PathHunter CHO-K1 MR cells Cat #93-0456C2, Lot No: 09B0913, from operation liquid nitrogen stock.
6. Control Antagonist: Spironolactone: Sigma #S-3378 and Eplerenone Sigma #107724-20-9 (10 mM stock concentration also prepared in DMSO and stored at −20° C.).

Methods:
Assay Set Up and Calculations:
1. Cells were grown in F12+FBS+Hygromycin+pen/strep+Genetin
2. Cells were collected with 0.05% trypsin and the cell suspension was spun and resuspended in a volume of F12+1.5% CD-FBS and counted.
3. The cells were resuspended to $4\times10^5$ cells/mL.
4. Cells were (25 µL/well) added to the wells of a 384 well plate.
5. The plate was then incubated at 37° C. over night in a humidified incubator with 5% $CO_2$.
6. Test compounds were titrated starting at 4.4 mM, 10-point titration in 1:3 dilution.
7. Aldosterone was diluted in assay media to 1.8 nM or 6 nM from 10 µM stock (final concentration to be about 0.3 nM to about 1.0 nM)

Protocol for 384 well plate format: 6 hr treatment:
1. Plated 10K exponentially growing cells/well (25 µL) resuspended in assay media to each well using the Multidrop (Thermo Electron) (use white wall, clear bottom assay plates (Costar #3570) and incubate overnight at 37° C., 5% $CO_2$.
2. 0.25 µL 120× test compound (final DMSO concentration should be <1%) was added to each well n=2, 10 point titrations starting at 36.7 µM final concentration.
3. 5 µL 6× agonist (final aldosterone concentration should be about 0.3 nM to about 1.0 nM) was added to all wells using the PlateMate Plus. (ThermoFisher) (except those wells in columns 23 and 24)
4. 5 µL of assay media was added to all wells in column 23 and 24.
5. Plates were incubated 6 hrs at 37° C., 5% $CO_2$.
6. 15 µL 3× DiscoveRx detection reagent was added to each well.
7. Plates were incubated for 1 hour at room temperature (plates stored in the dark).
8. Plates were read on Envision (PerkinElmer) luminesence plate reader and analyzed using ADA.

LC/MS method: (LC2M_Low/Medpositive mode).
LC Conditions: 5-98% $CH_3CN/H_2O$+v 0.1% TFA over 1.25 min; Flow Rate=1.5 mL/min, UV wavelength 254 nm; Column: Waters XTerra® MS C18 3.5 µm 2.1×20 mm IS™

As seen in the Examples above, compounds of the instant invention that had an $IC_{50}$ value greater than 0 nM but less than 100 nM were given an "A" $IC_{50}$ rating. Compounds of the instant invention that had an $IC_{50}$ value equal to, or greater than, 100 nM, but less than 500 nM, were given a "B" rating. Compounds of the instant invention that had an $IC_{50}$ value equal to, or greater than 500 nM, but less than 2,000 nM, were given a "C" rating.

What is claimed is:

1. A compound of Formula I:

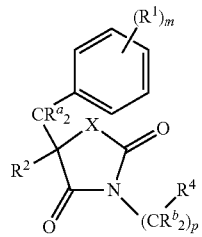

I or a pharmaceutically acceptable salt thereof, wherein
X is NH or O;
Each $R^1$ is independently halo, $CF_3$, $C_1$-$C_6$ alkyl, $C_3$-$C_{10}$ cycloalkyl, or OR, wherein said alkyl and cycloalkyl are optionally substituted with one to three groups selected from halo, OR, $CF_3$, or CN;
Each R is independently H, $C_1$-$C_6$ alkyl, $C_3$-$C_{10}$ cycloalkyl, or $CF_3$ wherein said alkyl and cycloalkyl are optionally substituted with one to three groups selected from halo, OH, $C_1$-$C_6$ alkoxy, $CF_3$, or CN;
Each $R^a$ is independently H, $C_1$-$C_6$ alkyl, $C_3$-$C_{10}$cycloalkyl, or $CF_3$ wherein said alkyl and cycloalkyl are optionally substituted with one to three groups selected from halo, OR, $CF_3$, or CN;
Each $R^b$ is independently H, $C_1$-$C_6$ alkyl, $C_3$-$C_{10}$ cycloalkyl, $CF_3$, or aryl, wherein said alkyl, cycloalkyl and aryl are optionally substituted with one to three groups selected from halo, OR, $CF_3$, or CN;
$R^2$ is triazolyl, oxadiazolyl, imidazolyl, thiazolyl, pyrazolyl, isoxazolyl, thiadiazolyl or oxazolyl, where triazolyl, oxadiazolyl, imidazolyl, thiazolyl, pyrazolyl, isoxazolyl, thiadiazolyl or oxazolyl is optionally substituted with one to two groups from $R^5$;
$R^4$ is H, $C_1$-$C_6$ alkyl, aryl, or $C_3$-$C_{10}$ cycloalkyl, where said alkyl, aryl, or cycloalkyl is optionally substituted with one to four groups selected from halo or OR;
Each $R^5$ is independently OR, $(CR^c_2)_{0-3}$—$CF_3$, $C_1$-$C_6$ alkyl, $(CR^c_2)_{0-3}$—$C_3$-$C_{10}$ cycloalkyl, $(CR^c_2)_{0-3}$-aryl, $(CR^c_2)_{0-3}$-heteroaryl, or $(CR^c_2)_{0-3}$-halo, where said alkyl, cycloalkyl, aryl or heteroaryl is optionally substituted with one to three groups selected from optionally substituted aryl, optionally substituted heteroaryl, optionally substituted heterocyclyl, OR, halo, $CF_3$ or $NH_2$; and wherein said optionally substituted aryl, optionally substituted heteroaryl, or optionally substituted heterocyclyl are optionally substituted one to four times by halo, $CF_3$, $NH_2$ or OR;
Each $R^c$ is independently H, $C_1$-$C_6$ alkyl, or $C_3$-$C_{10}$ cycloalkyl, wherein said alkyl and cycloalkyl are optionally substituted with one to three groups selected from halo, OR, $CF_3$, or CN;
m is 0, 1, 2 or 3; and
p is 0, 1, 2 or 3.

2. The compound of Formula I, according to claim 1, wherein
Each $R^a$ is independently H or $C_1$-$C_6$ alkyl wherein said alkyl is optionally substituted with one to three groups selected from halo, OR, $CF_3$, or CN;
$R^2$ is triazolyl, oxadiazolyl, imidazolyl or oxazolyl, where triazolyl, oxadiazolyl, imidazolyl or oxazolyl is optionally substituted with one to two groups from $R^5$;
$R^4$ is aryl or $C_3$-$C_{10}$ cycloalkyl, where said aryl or cycloalkyl is optionally substituted with one to four groups selected from halo or OR;
Each $R^5$ is independently OR, $C_1$-$C_6$ alkyl, $(CR^c_2)_{0-3}$—$C_3$-$C_{10}$ cycloalkyl, $(CR^c_2)_{0-3}$-aryl, $(CR^c_2)_{0-3}$-heteroaryl, or $(CR^c_2)_{0-3}$-halo, where said alkyl, cycloalkyl, aryl or heteroaryl is optionally substituted with one to three groups selected from aryl, heteroaryl, or heterocyclyl;
m is 0 or 1; and
p is 0, 1 or 2;
or a pharmaceutically acceptable salt thereof.

3. A compound of Formula II:

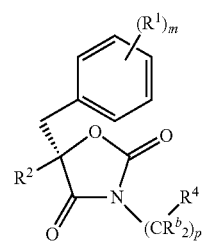

II or a pharmaceutically acceptable salt thereof, wherein
Each $R^1$ is independently halo, $CF_3$, $C_1$-$C_6$ alkyl, $C_3$-$C_{10}$ cycloalkyl, or OR, wherein said alkyl and cycloalkyl are optionally substituted with one to three groups selected from halo, OR, $CF_3$, or CN;
Each R is independently H, $C_1$-$C_6$ alkyl, $C_3$-$C_{10}$ cycloalkyl, or $CF_3$ wherein said alkyl and cycloalkyl are optionally substituted with one to three groups selected from halo, OR, $CF_3$, or CN;
Each $R^b$ is independently H or $C_1$-$C_6$ alkyl, wherein said alkyl is optionally substituted with one to three groups selected from halo, OR, $CF_3$, or CN;
Each $R^c$ is independently H, $C_1$-$C_6$ alkyl, or $C_3$-$C_{10}$ cycloalkyl, wherein said alkyl and cycloalkyl are optionally substituted with one to three groups selected from halo, OR, $CF_3$, or CN;
$R^2$ is triazolyl, oxadiazolyl, imidazolyl or oxazolyl, where triazolyl, oxadiazolyl, imidazolyl or oxazolyl is optionally substituted with one to two groups from $R^5$;
$R^4$ is $C_1$-$C_6$ alkyl, aryl, or $C_3$-$C_{10}$ cycloalkyl, where said alkyl, aryl, or cycloalkyl is optionally substituted with one to four groups selected from halo or OR;
Each $R^5$ is independently $(CR^c_2)_{0-3}$—$CF_3$, $C_1$-$C_6$ alkyl, $(CR^c_2)_{0-3}$—$C_3$-$C_1$ cycloalkyl, $(CR^c_2)_{0-3}$aryl, $(CR^c_2)_{0-3}$-heteroaryl, or $(CR^c_2)_{0-3}$-halo, where said alkyl, cycloalkyl, aryl or heteroaryl is optionally substituted with one to three groups selected from aryl, heteroaryl, heterocyclyl, OR, halo, $CF_3$ or $NH_2$;
m is 0 or 1; and
p is 1 or 2.

4. The compound of claim 3, having the structural Formula II, wherein
Each $R^b$ is independently H or $C_1$-$C_6$ alkyl;
$R^4$ is aryl, or $C_3$-$C_{10}$ cycloalkyl, where said aryl, or cycloalkyl is optionally substituted with one to four groups selected from halo or OR;
Each $R^5$ is independently $(CR^c_2)_{0-3}$—$C_3$-$C_{10}$ cycloalkyl, $(CR^c_2)_{0-3}$-aryl, or $(CR^c_2)_{0-3}$-heteroaryl, where said cycloalkyl, aryl or heteroaryl is optionally substituted with one to three groups selected from aryl, heteroaryl, heterocyclyl, OR, halo, $CF_3$ or $NH_2$; and
p is 1;
or a pharmaceutically acceptable salt thereof.

5. A compound which is

| Compound Number | IUPAC Name |
| --- | --- |
| 1 | 5-Benzyl-5-[5-(3,5-dimethoxyphenyl)-4H-1,2,4-triazol-3-yl]-3-[(1R)-1-(4-fluorophenyl)ethyl]-1,3-oxazolidine-2,4-dione |
| 2 | (5R)-5-Benzyl-5-[5-(3,5-dimethoxybenzyl)-1,3,4-oxadiazol-2-yl]-3-[(1R)-1-phenylethyl]-1,3-oxazolidine-2,4-dione |
| 3 | (5R)-5-Benzyl-5-(5-benzyl-1,3,4-oxadiazol-2-yl)-3-[(1R)-1-phenylethyl]-1,3-oxazolidine-2,4-dione |
| 4 | (5R)-5-Benzyl-5-[5-(3,5-dimethoxyphenyl)-1,3,4-oxadiazol-2-yl]-3-[(1R)-1-phenylethyl]-1,3-oxazolidine-2,4-dione |
| 5 | (5R)-5-Benzyl-5-[5-(1-phenylcyclopropyl)-1,3,4-oxadiazol-2-yl]-3-[(1R)-1-phenylethyl]-1,3-oxazolidine-2,4-dione |
| 6 | (5R)-5-Benzyl-3-[(1R)-1-phenylethyl]-5-(3-phenyl-1,2,4-oxadiazol-5-yl)-1,3-oxazolidine-2,4-dione |
| 7 | (5R)-5-Benzyl-3-[(1R)-1-phenylethyl]-5-(5-pyridin-4-yl-1,3,4-oxadiazol-2-yl)-1,3-oxazolidine-2,4-dione |
| 8 | (5R)-5-Benzyl-5-[5-(4,6-dimethoxypyrimidin-2-yl)-1,3,4-oxadiazol-2-yl]-3-[(1R)-1-phenylethyl]-1,3-oxazolidine-2,4-dione |
| 9 | (5R)-5-Benzyl-5-{5-[1-(3,5-difluorophenyl)cyclopropyl]-1,3,4-oxadiazol-2-yl}-3-[(1R)-1-phenylethyl]-1,3-oxazolidine-2,4-dione |
| 10 | (5R)-5-[5-(3-Amino-5-methoxyphenyl)-1,3,4-oxadiazol-2-yl]-5-benzyl-3-[(1R)-1-phenylethyl]-1,3-oxazolidine-2,4-dione |
| 11 | (5R)-5-Benzyl-3-[(1R)-1-phenylethyl]-5-[5-(2,2,2-trifluoroethyl)-1,3,4-oxadiazol-2-yl]-1,3-oxazolidine-2,4-dione |
| 12 | (5R)-5-Benzyl-3-[(1R)-1-phenylethyl]-5-{5-[1-(trifluoromethyl)cyclopropyl]-1,3,4-oxadiazol-2-yl}-1,3-oxazolidine-2,4-dione |
| 13 | (5R)-5-Benzyl-5-[5-(cyclopropylmethyl)-1,3,4-oxadiazol-2-yl]-3-[(1R)-1-phenylethyl]-1,3-oxazolidine-2,4-dione |
| 14 | (5R)-5-Benzyl-3-[(1R)-1-phenylethyl]-5-[5-(1-pyridin-4-ylcyclopropyl)-1,3,4-oxadiazol-2-yl]-1,3-oxazolidine-2,4-dione |
| 15 | (5R)-5-Benzyl-5-[4-(3,5-dimethoxyphenyl)-1H-imidazol-2-yl]-3-[(1R)-1-phenylethyl]-1,3-oxazolidine-2,4-dione |
| 16 | (5R)-5-Benzyl-3-[(1R)-1-phenylethyl]-5-(5-phenyl-1H-imidazol-2-yl)-1,3-oxazolidine-2,4-dione |
| 17 | (5R)-5-Benzyl-5-(5-benzyl-1H-imidazol-2-yl)-3-[(1R)-1-phenylethyl]-1,3-oxazolidine-2,4-dione |
| 18 | (5R)-5-Benzyl-3-[(1R)-1-phenylethyl]-5-(4-phenyl-1,3-oxazol-2-yl)-1,3-oxazolidine-2,4-dione |
| 19 | (5R)-5-Benzyl-3-[(1R)-1-phenylethyl]-5-(5-phenyl-1,3-oxazol-2-yl)-1,3-oxazolidine-2,4-dione |
| 20 | (5R)-5-Benzyl-5-(5-benzyl-1,3-oxazol-2-yl)-3-[(1R)-1-phenylethyl]-1,3-oxazolidine-2,4-dione |
| 21 | (5R)-5-Benzyl-3-[(1R)-1-phenylethyl]-5-(3-phenyl-1H-1,2,4-triazol-5-yl)-1,3-oxazolidine-2,4-dione |
| 22 | (5R)-5-Benzyl-5-[5-(3,5-dimethoxyphenyl)-1,3,4-oxadiazol-2-yl]-3-[(1R)-1-phenylethyl]imidazolidine-2,4-dione | or a pharmaceutically acceptable salt thereof.

6. The compound of claim 5, which is

| Compound Number | IUPAC Name |
| --- | --- |
| 1 | 5-Benzyl-5-[5-(3,5-dimethoxyphenyl)-4H-1,2,4-triazol-3-yl]-3-[(1R)-1-(4-fluorophenyl)ethyl]-1,3-oxazolidine-2,4-dione |
| 2 | (5R)-5-Benzyl-5-[5-(3,5-dimethoxybenzyl)-1,3,4-oxadiazol-2-yl]-3-[(1R)-1-phenylethyl]-1,3-oxazolidine-2,4-dione |
| 3 | (5R)-5-Benzyl-5-(5-benzyl-1,3,4-oxadiazol-2-yl)-3-[(1R)-1-phenylethyl]-1,3-oxazolidine-2,4-dione |
| 4 | (5R)-5-Benzyl-5-[5-(3,5-dimethoxyphenyl)-1,3,4-oxadiazol-2-yl]-3-[(1R)-1-phenylethyl]-1,3-oxazolidine-2,4-dione |
| 5 | (5R)-5-Benzyl-5-[5-(1-phenylcyclopropyl)-1,3,4-oxadiazol-2-yl]-3-[(1R)-1-phenylethyl]-1,3-oxazolidine-2,4-dione |
| 8 | (5R)-5-Benzyl-5-[5-(4,6-dimethoxypyrimidin-2-yl)-1,3,4-oxadiazol-2-yl]-3-[(1R)-1-phenylethyl]-1,3-oxazolidine-2,4-dione |
| 13 | (5R)-5-Benzyl-5-[5-(cyclopropylmethyl)-1,3,4-oxadiazol-2-yl]-3-[(1R)-1-phenylethyl]-1,3-oxazolidine-2,4-dione |
| 15 | (5R)-5-Benzyl-5-[4-(3,5-dimethoxyphenyl)-1H-imidazol-2-yl]-3-[(1R)-1-phenylethyl]-1,3-oxazolidine-2,4-dione |
| 22 | (5R)-5-Benzyl-5-[5-(3,5-dimethoxyphenyl)-1,3,4-oxadiazol-2-yl]-3-[(1R)-1-phenylethyl]imidazolidine-2,4-dione | or a pharmaceutically acceptable salt thereof.

7. A pharmaceutical composition comprised of the compound of Formula I of claim 1, or a pharmaceutically acceptable salt thereof, and a pharmaceutically acceptable carrier.

8. The pharmaceutical composition of claim 7 comprising one or more pharmaceutically active agents in addition to the compound of Formula I or a pharmaceutically acceptable salt thereof.

9. A method of treating heart failure, hypertension, atherosclerosis or primary hyperaldosteronism in a human patient in need of, comprising administering to the patient a therapeutically effective amount of a compound of claim 1 or a pharmaceutically acceptable salt thereof.

10. A method of treating metabolic syndrome in a mammal in need of such treatment, comprising administering to the mammal a therapeutically effective amount of a compound of claim 1 or a pharmaceutically acceptable salt thereof.

11. A method of treating a physiological or pathologic disease, selected from Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, and Bartter's Syndrome in a human patient in need of, comprising administering to the patient a therapeutically effective amount of a compound of claim 1 or a pharmaceutically acceptable salt thereof.

12. A method of treating renal failure in a human patient in need of such treatment comprising administering to the patient a therapeutically effective amount of a compound of claim 1 or a pharmaceutically acceptable salt thereof.

13. A method for antagonizing aldosterone receptor (MR) and increasing aldosterone levels in a mammal in need thereof which comprises administering to said mammal a therapeutically effective amount of a compound of claim 1 or a pharmaceutically acceptable salt thereof.

* * * * *